US011443649B2

(12) United States Patent
Cadwell et al.

(10) Patent No.: US 11,443,649 B2
(45) Date of Patent: Sep. 13, 2022

(54) NEUROPHYSIOLOGICAL MONITORING TRAINING SIMULATOR

(71) Applicant: Cadwell Laboratories, Inc., Kennewick, WA (US)

(72) Inventors: John A. Cadwell, Richland, WA (US); Melissa Miles, West Linn, OR (US); Mark Romero, Richland, WA (US)

(*) Notice: Subject to any disclaimer, the term of this patent is extended or adjusted under 35 U.S.C. 154(b) by 385 days.

(21) Appl. No.: 16/455,774

(22) Filed: Jun. 28, 2019

(65) Prior Publication Data
US 2020/0160741 A1 May 21, 2020

Related U.S. Application Data

(60) Provisional application No. 62/692,539, filed on Jun. 29, 2018.

(51) Int. Cl.
*G09B 23/28* (2006.01)
*G09B 9/00* (2006.01)
*A61B 34/10* (2016.01)
*A61B 5/00* (2006.01)
A61B 5/318 (2021.01)
A61B 5/389 (2021.01)

(52) U.S. Cl.
CPC .............. *G09B 9/00* (2013.01); *A61B 5/4041* (2013.01); *A61B 34/10* (2016.02); *A61B 5/318* (2021.01); *A61B 5/389* (2021.01); *A61B 5/7207* (2013.01); *A61B 5/7217* (2013.01); *A61B 2034/101* (2016.02); *A61B 2505/05* (2013.01)

(58) Field of Classification Search
CPC ................................ G09B 23/28; G09B 23/30
See application file for complete search history.

(56) References Cited

U.S. PATENT DOCUMENTS 751,475 A 2/1904 Vilbiss
972,983 A 10/1910 Arthur
(Continued)

FOREIGN PATENT DOCUMENTS

AT 466451 T 5/2010
AT 539680 T 1/2012
(Continued)

OTHER PUBLICATIONS

Cadwell et al. "Electrophysiologic Equipment and Electrical Safety" Chapter 2, Electrodiagnosis in Clinical Neurology, Fourth Edition; Churchill Livingstone, p. 15, 30-31; 1999.
(Continued)

*Primary Examiner* — Kurt Fernstrom
(74) *Attorney, Agent, or Firm* — Novel IP

(57) ABSTRACT

A training simulator for intraoperative neuromonitoring (IONM) systems includes channels where at least one of the channels is identified as an active stimulation channel and a subset of the rest of the channels is identified as reference or pick up sites. Channels of the subset having signal data that exceed a predefined threshold are retained for further processing, while channels with signal data that do not exceed the threshold are eliminated from further reporting. Response data for the remaining channels are generated in advance of a future time when the response would occur. The generated data is time stamped and stored for display at a time window when requested by the system.

24 Claims, 16 Drawing Sheets

(56) References Cited

U.S. PATENT DOCUMENTS

| | | |
|---|---|---|
| 1,328,624 A | 1/1920 | Graham |
| 1,477,527 A | 12/1923 | Raettig |
| 1,548,184 A | 8/1925 | Cameron |
| 1,717,480 A | 6/1929 | Wappler |
| 1,842,323 A | 1/1932 | Lorand |
| 2,110,735 A | 3/1938 | Marton |
| 2,320,709 A | 6/1943 | Arnesen |
| 2,516,882 A | 8/1950 | Kalom |
| 2,704,064 A | 3/1955 | Fizzell |
| 2,736,002 A | 2/1956 | Oriel |
| 2,807,259 A | 9/1957 | Federico |
| 2,808,826 A | 10/1957 | Reiner |
| 2,994,324 A | 8/1961 | Lemos |
| 3,035,580 A | 5/1962 | Guiorguiev |
| 3,057,356 A | 10/1962 | Greatbatch |
| 3,060,923 A | 10/1962 | Reiner |
| 3,087,486 A | 4/1963 | Kilpatrick |
| 3,147,750 A | 9/1964 | Fry |
| 3,188,605 A | 6/1965 | Slenker |
| 3,212,496 A | 10/1965 | Preston |
| 3,219,029 A | 11/1965 | Richards |
| 3,313,293 A | 4/1967 | Chesebrough |
| 3,364,929 A | 1/1968 | Ide |
| 3,580,242 A | 5/1971 | La |
| 3,611,262 A | 10/1971 | Marley |
| 3,617,616 A | 11/1971 | O'Loughlin |
| 3,641,993 A | 2/1972 | Gaarder |
| 3,646,500 A | 2/1972 | Wessely |
| 3,651,812 A | 3/1972 | Samuels |
| 3,662,744 A | 5/1972 | Richardson |
| 3,664,329 A | 5/1972 | Naylor |
| 3,682,162 A | 8/1972 | Colyer |
| 3,703,900 A | 11/1972 | Holznagel |
| 3,718,132 A | 2/1973 | Holt |
| 3,733,574 A | 5/1973 | Scoville |
| 3,785,368 A | 1/1974 | McCarthy |
| 3,830,226 A | 8/1974 | Staub |
| 3,857,398 A | 12/1974 | Rubin |
| 3,880,144 A | 4/1975 | Coursin |
| 3,933,157 A | 1/1976 | Bjurwill |
| 3,957,036 A | 5/1976 | Normann |
| 3,960,141 A | 6/1976 | Bolduc |
| 3,985,125 A | 10/1976 | Rose |
| 4,062,365 A | 12/1977 | Kameny |
| 4,088,141 A | 5/1978 | Niemi |
| 4,099,519 A | 7/1978 | Warren |
| 4,127,312 A | 11/1978 | Fleischhacker |
| 4,141,365 A | 2/1979 | Fischell |
| 4,155,353 A | 5/1979 | Rea |
| 4,164,214 A | 8/1979 | Pelzner |
| 4,175,551 A | 11/1979 | Haenensirnee |
| 4,177,799 A | 12/1979 | Masreliez |
| 4,184,492 A | 1/1980 | Fastenmeier |
| 4,200,104 A | 4/1980 | Harris |
| 4,204,545 A | 5/1980 | Yamakoshi |
| 4,207,897 A | 6/1980 | Evatt |
| 4,224,949 A | 9/1980 | Scott |
| 4,226,228 A | 10/1980 | Shin |
| 4,232,680 A | 11/1980 | Hudleson |
| 4,233,987 A | 11/1980 | Feingold |
| 4,235,242 A | 11/1980 | Heule |
| 4,263,899 A | 4/1981 | Burgin |
| 4,265,237 A | 5/1981 | Schwanbom |
| 4,285,347 A | 8/1981 | Hess |
| 4,291,705 A | 9/1981 | Severinghaus |
| 4,294,245 A | 10/1981 | Bussey |
| 4,295,703 A | 10/1981 | Osborne |
| 4,299,230 A | 11/1981 | Kubota |
| 4,308,012 A | 12/1981 | Tamler |
| 4,331,157 A | 5/1982 | Keller, Jr. |
| 4,372,319 A | 2/1983 | Ichinomiya |
| 4,373,531 A | 2/1983 | Wittkampf |
| 4,374,517 A | 2/1983 | Hagiwara |
| 4,402,323 A | 9/1983 | White |
| 4,444,187 A | 4/1984 | Perlin |
| 4,461,300 A | 7/1984 | Christensen |
| 4,469,098 A | 9/1984 | Davi |
| 4,483,338 A | 11/1984 | Bloom |
| 4,485,823 A | 12/1984 | Yamaguchi |
| 4,487,489 A | 12/1984 | Takamatsu |
| 4,503,842 A | 3/1985 | Takayama |
| 4,503,863 A | 3/1985 | Katims |
| 4,510,939 A | 4/1985 | Brenman |
| 4,515,168 A | 5/1985 | Chester |
| 4,517,976 A | 5/1985 | Murakoshi |
| 4,517,983 A | 5/1985 | Yasuhiro |
| 4,519,403 A | 5/1985 | Dickhudt |
| 4,537,198 A | 8/1985 | Corbett |
| 4,545,374 A | 10/1985 | Jacobson |
| 4,557,273 A | 12/1985 | Stoller |
| 4,558,703 A | 12/1985 | Mark |
| 4,561,445 A | 12/1985 | Berke |
| 4,562,832 A | 1/1986 | Wilder |
| 4,565,200 A | 1/1986 | Cosman |
| 4,570,640 A | 2/1986 | Barsa |
| 4,573,448 A | 3/1986 | Kambin |
| 4,573,449 A | 3/1986 | Warnke |
| 4,576,178 A | 3/1986 | Johnson |
| 4,582,063 A | 4/1986 | Mickiewicz |
| 4,592,369 A | 6/1986 | Davis |
| 4,595,018 A | 6/1986 | Rantala |
| 4,616,635 A | 10/1986 | Caspar |
| 4,616,660 A | 10/1986 | Johns |
| 4,622,973 A | 11/1986 | Agarwala |
| 4,633,889 A | 1/1987 | Talalla |
| 4,641,661 A | 2/1987 | Kalarickal |
| 4,643,507 A | 2/1987 | Coldren |
| 4,658,835 A | 4/1987 | Pohndorf |
| 4,667,676 A | 5/1987 | Guinta |
| 4,697,598 A | 10/1987 | Bernard |
| 4,697,599 A | 10/1987 | Woodley |
| 4,705,049 A | 11/1987 | John |
| 4,716,901 A | 1/1988 | Jackson |
| 4,739,772 A | 4/1988 | Hokanson |
| 4,744,371 A | 5/1988 | Harris |
| 4,759,377 A | 7/1988 | Dykstra |
| 4,763,666 A | 8/1988 | Strian |
| 4,765,311 A | 8/1988 | Kulik |
| 4,784,150 A | 11/1988 | Voorhies |
| 4,785,812 A | 11/1988 | Pihl |
| 4,795,998 A | 1/1989 | Dunbar |
| 4,807,642 A | 2/1989 | Brown |
| 4,807,643 A | 2/1989 | Rosier |
| 4,817,587 A | 4/1989 | Janese |
| 4,817,628 A | 4/1989 | Zealear |
| 4,827,935 A | 5/1989 | Geddes |
| 4,841,973 A | 6/1989 | Stecker |
| 4,844,091 A | 7/1989 | Bellak |
| 4,862,891 A | 9/1989 | Smith |
| 4,892,105 A | 1/1990 | Prass |
| 4,895,152 A | 1/1990 | Callaghan |
| 4,920,968 A | 5/1990 | Takase |
| 4,926,865 A | 5/1990 | Oman |
| 4,926,880 A | 5/1990 | Claude |
| 4,934,377 A | 6/1990 | Bova |
| 4,934,378 A | 6/1990 | Perry, Jr. |
| 4,934,957 A | 6/1990 | Bellusci |
| 4,962,766 A | 10/1990 | Herzon |
| 4,964,411 A | 10/1990 | Johnson |
| 4,964,811 A | 10/1990 | Hayes, Sr. |
| 4,984,578 A | 1/1991 | Keppel |
| 4,998,796 A | 3/1991 | Bonanni |
| 5,007,902 A | 4/1991 | Witt |
| 5,015,247 A | 5/1991 | Michelson |
| 5,018,526 A | 5/1991 | Gaston-Johansson |
| 5,020,542 A | 6/1991 | Rossmann |
| 5,024,228 A | 6/1991 | Goldstone |
| 5,058,602 A | 10/1991 | Brody |
| 5,080,606 A | 1/1992 | Burkard |
| 5,081,990 A | 1/1992 | DeLetis |
| 5,085,226 A | 2/1992 | DeLuca |
| 5,092,344 A | 3/1992 | Lee |
| 5,095,905 A | 3/1992 | Klepinski |
| 5,125,406 A | 6/1992 | Goldstone |

(56) References Cited

U.S. PATENT DOCUMENTS

| | | |
|---|---|---|
| 5,127,403 A | 7/1992 | Brownlee |
| 5,131,389 A | 7/1992 | Giordani |
| 5,143,081 A | 9/1992 | Young |
| 5,146,920 A | 9/1992 | Takahiro |
| 5,161,533 A | 11/1992 | Prass |
| 5,163,328 A | 11/1992 | Holland |
| 5,171,279 A | 12/1992 | Mathews |
| 5,190,048 A | 3/1993 | Wilkinson |
| 5,191,896 A | 3/1993 | Gafni |
| 5,195,530 A | 3/1993 | Shindel |
| 5,195,532 A | 3/1993 | Schumacher |
| 5,196,015 A | 3/1993 | Neubardt |
| 5,199,899 A | 4/1993 | Ittah |
| 5,201,325 A | 4/1993 | McEwen |
| 5,215,100 A | 6/1993 | Spitz |
| RE34,390 E | 9/1993 | Culver |
| 5,253,656 A | 10/1993 | Rincoe |
| 5,255,691 A | 10/1993 | Otten |
| 5,277,197 A | 1/1994 | Church |
| 5,282,468 A | 2/1994 | Klepinski |
| 5,284,153 A | 2/1994 | Raymond |
| 5,284,154 A | 2/1994 | Raymond |
| 5,292,309 A | 3/1994 | Van Tassel |
| 5,299,563 A | 4/1994 | Seton |
| 5,306,236 A | 4/1994 | Blumenfeld |
| 5,312,417 A | 5/1994 | Wilk |
| 5,313,956 A | 5/1994 | Knutsson |
| 5,313,962 A | 5/1994 | Obenchain |
| 5,327,902 A | 7/1994 | Lemmen |
| 5,333,618 A | 8/1994 | Lekhtman |
| 5,343,871 A | 9/1994 | Bittman |
| 5,347,989 A | 9/1994 | Monroe |
| 5,358,423 A | 10/1994 | Burkhard |
| 5,358,514 A | 10/1994 | Schulman |
| 5,368,043 A | 11/1994 | Sunouchi |
| 5,373,317 A | 12/1994 | Salvati |
| 5,375,067 A | 12/1994 | Berchin |
| 5,377,667 A | 1/1995 | Patton |
| 5,381,805 A | 1/1995 | Tuckett |
| 5,383,876 A | 1/1995 | Nardella |
| 5,389,069 A | 2/1995 | Weaver |
| 5,405,365 A | 4/1995 | Hoegnelid |
| 5,413,111 A | 5/1995 | Wilkinson |
| 5,454,365 A | 10/1995 | Bonutti |
| 5,470,349 A | 11/1995 | Kleditsch |
| 5,472,426 A | 12/1995 | Bonati |
| 5,474,558 A | 12/1995 | Neubardt |
| 5,480,440 A | 1/1996 | Kambin |
| 5,482,038 A | 1/1996 | Ruff |
| 5,484,437 A | 1/1996 | Michelson |
| 5,485,852 A | 1/1996 | Johnson |
| 5,491,299 A | 2/1996 | Naylor |
| 5,514,005 A | 5/1996 | Jaycox |
| 5,514,165 A | 5/1996 | Malaugh |
| 5,522,386 A | 6/1996 | Lerner |
| 5,540,235 A | 7/1996 | Wilson |
| 5,549,656 A | 8/1996 | Reiss |
| 5,560,372 A | 10/1996 | Cory |
| 5,565,779 A | 10/1996 | Arakawa |
| 5,566,678 A | 10/1996 | Cadwell |
| 5,569,248 A | 10/1996 | Mathews |
| 5,575,284 A | 11/1996 | Athan |
| 5,579,781 A | 12/1996 | Cooke |
| 5,591,216 A | 1/1997 | Testerman |
| 5,593,429 A | 1/1997 | Ruff |
| 5,599,279 A | 2/1997 | Slotman |
| 5,601,608 A | 2/1997 | Mouchawar |
| 5,618,208 A | 4/1997 | Crouse |
| 5,620,483 A | 4/1997 | Minogue |
| 5,622,515 A | 4/1997 | Hotea |
| 5,630,813 A | 5/1997 | Kieturakis |
| 5,634,472 A | 6/1997 | Puthalath |
| 5,671,752 A | 9/1997 | Sinderby |
| 5,681,265 A | 10/1997 | Maeda |
| 5,687,080 A | 11/1997 | Hoyt |
| 5,707,359 A | 1/1998 | Bufalini |
| 5,711,307 A | 1/1998 | Smits |
| 5,725,514 A | 3/1998 | Grinblat |
| 5,728,046 A | 3/1998 | Mayer |
| 5,741,253 A | 4/1998 | Michelson |
| 5,741,261 A | 4/1998 | Moskovitz |
| 5,759,159 A | 6/1998 | Masreliez |
| 5,769,781 A | 6/1998 | Chappuis |
| 5,772,597 A | 6/1998 | Goldberger |
| 5,772,661 A | 6/1998 | Michelson |
| 5,775,331 A | 7/1998 | Raymond |
| 5,776,144 A | 7/1998 | Leysieffer |
| 5,779,642 A | 7/1998 | Nightengale |
| 5,785,648 A | 7/1998 | Min |
| 5,785,658 A | 7/1998 | Benaron |
| 5,792,044 A | 8/1998 | Foley |
| 5,795,291 A | 8/1998 | Koros |
| 5,797,854 A | 8/1998 | Hedgecock |
| 5,806,522 A | 9/1998 | Katims |
| 5,814,073 A | 9/1998 | Bonutti |
| 5,830,150 A | 11/1998 | Palmer |
| 5,830,151 A | 11/1998 | Hadzic |
| 5,833,714 A | 11/1998 | Loeb |
| 5,836,880 A | 11/1998 | Pratt |
| 5,851,191 A | 12/1998 | Gozani |
| 5,853,373 A | 12/1998 | Griffith |
| 5,857,986 A | 1/1999 | Moriyasu |
| 5,860,829 A | 1/1999 | Hower |
| 5,860,973 A | 1/1999 | Michelson |
| 5,862,314 A | 1/1999 | Jeddeloh |
| 5,868,668 A | 2/1999 | Weiss |
| 5,872,314 A | 2/1999 | Clinton |
| 5,885,210 A | 3/1999 | Cox |
| 5,885,219 A | 3/1999 | Nightengale |
| 5,888,196 A | 3/1999 | Bonutti |
| 5,891,147 A | 4/1999 | Moskovitz |
| 5,895,298 A | 4/1999 | Faupel |
| 5,902,231 A | 5/1999 | Foley |
| 5,924,984 A | 7/1999 | Rao |
| 5,928,030 A | 7/1999 | Daoud |
| 5,928,139 A | 7/1999 | Koros |
| 5,928,158 A | 7/1999 | Aristides |
| 5,931,777 A | 8/1999 | Sava |
| 5,944,658 A | 8/1999 | Koros |
| 5,954,635 A | 9/1999 | Foley |
| 5,954,716 A | 9/1999 | Sharkey |
| 5,993,385 A | 11/1999 | Johnston |
| 5,993,434 A | 11/1999 | Dev |
| 6,004,262 A | 12/1999 | Putz |
| 6,004,312 A | 12/1999 | Finneran |
| 6,004,341 A | 12/1999 | Zhu |
| 6,009,347 A | 12/1999 | Hofmann |
| 6,011,985 A | 1/2000 | Athan |
| 6,027,456 A | 2/2000 | Feler |
| 6,029,090 A | 2/2000 | Herbst |
| 6,038,469 A | 3/2000 | Karlsson |
| 6,038,477 A | 3/2000 | Kayyali |
| 6,042,540 A | 3/2000 | Johnston |
| 6,050,992 A | 4/2000 | Nichols |
| 6,074,343 A | 6/2000 | Nathanson |
| 6,077,237 A | 6/2000 | Campbell |
| 6,095,987 A | 8/2000 | Shmulewitz |
| 6,104,957 A | 8/2000 | Alo |
| 6,104,960 A | 8/2000 | Duysens |
| 6,119,068 A | 9/2000 | Kannonji |
| 6,120,503 A | 9/2000 | Michelson |
| 6,126,660 A | 10/2000 | Dietz |
| 6,128,576 A | 10/2000 | Nishimoto |
| 6,132,386 A | 10/2000 | Gozani |
| 6,132,387 A | 10/2000 | Gozani |
| 6,135,965 A | 10/2000 | Tumer |
| 6,139,493 A | 10/2000 | Koros |
| 6,139,545 A | 10/2000 | Utley |
| 6,146,334 A | 11/2000 | Laserow |
| 6,146,335 A | 11/2000 | Gozani |
| 6,152,871 A | 11/2000 | Foley |
| 6,161,047 A | 12/2000 | King |
| 6,181,961 B1 | 1/2001 | Prass |
| 6,196,969 B1 | 3/2001 | Bester |

(56) References Cited

U.S. PATENT DOCUMENTS

| | | | |
|---|---|---|---|
| 6,206,826 B1 | 3/2001 | Mathews | |
| 6,210,324 B1 | 4/2001 | Reno | |
| 6,214,035 B1 | 4/2001 | Streeter | |
| 6,224,545 B1 | 5/2001 | Cocchia | |
| 6,224,549 B1 | 5/2001 | Drongelen | |
| 6,234,953 B1 | 5/2001 | Thomas | |
| 6,249,706 B1 | 6/2001 | Sobota | |
| 6,259,945 B1 | 7/2001 | Epstein | |
| 6,266,558 B1 | 7/2001 | Gozani | |
| 6,273,905 B1 | 8/2001 | Streeter | |
| 6,287,322 B1 | 9/2001 | Zhu | |
| 6,292,701 B1 | 9/2001 | Prass | |
| 6,298,256 B1 | 10/2001 | Meyer | |
| 6,302,842 B1 | 10/2001 | Auerbach | |
| 6,306,100 B1 | 10/2001 | Prass | |
| 6,309,349 B1 | 10/2001 | Bertolero | |
| 6,312,392 B1 | 11/2001 | Herzon | |
| 6,314,324 B1 | 11/2001 | Lattner | |
| 6,325,764 B1 | 12/2001 | Griffith | |
| 6,334,068 B1 | 12/2001 | Hacker | |
| 6,346,078 B1 | 2/2002 | Ellman | |
| 6,348,058 B1 | 2/2002 | Melkent | |
| 6,366,813 B1 | 4/2002 | DiLorenzo | |
| 6,391,005 B1 | 5/2002 | Lum | |
| 6,393,325 B1 | 5/2002 | Mann | |
| 6,425,859 B1 | 7/2002 | Foley | |
| 6,425,901 B1 | 7/2002 | Zhu | |
| 6,441,747 B1 | 8/2002 | Khair | |
| 6,450,952 B1 | 9/2002 | Rioux | |
| 6,451,015 B1 | 9/2002 | Rittman, III | |
| 6,461,352 B2 | 10/2002 | Morgan | |
| 6,466,817 B1 | 10/2002 | Kaula | |
| 6,487,446 B1 | 11/2002 | Hill | |
| 6,500,128 B2 | 12/2002 | Marino | |
| 6,500,173 B2 | 12/2002 | Underwood | |
| 6,500,180 B1 | 12/2002 | Foley | |
| 6,500,210 B1 | 12/2002 | Sabolich | |
| 6,507,755 B1 | 1/2003 | Gozani | |
| 6,511,427 B1 | 1/2003 | Sliwajr | |
| 6,535,759 B1 | 3/2003 | Epstein | |
| 6,543,299 B2 | 4/2003 | Taylor | |
| 6,546,271 B1 | 4/2003 | Reisfeld | |
| 6,564,078 B1 | 5/2003 | Marino | |
| 6,568,961 B1 | 5/2003 | Liburdi | |
| 6,572,545 B2 * | 6/2003 | Knobbe | A61B 5/0002 600/365 |
| 6,577,236 B2 | 6/2003 | Harman | |
| 6,579,244 B2 | 6/2003 | Goodwin | |
| 6,582,441 B1 | 6/2003 | He | |
| 6,585,638 B1 | 7/2003 | Yamamoto | |
| 6,609,018 B2 | 8/2003 | Cory | |
| 6,618,626 B2 | 9/2003 | West, Jr. | |
| 6,623,500 B1 | 9/2003 | Cook | |
| 6,638,101 B1 | 10/2003 | Botelho | |
| 6,692,258 B1 * | 2/2004 | Kurzweil | G09B 23/28 434/262 |
| 6,712,795 B1 | 3/2004 | Cohen | |
| 6,719,692 B2 | 4/2004 | Kleffner | |
| 6,730,021 B2 | 5/2004 | Vassiliades, Jr. | |
| 6,770,074 B2 | 8/2004 | Michelson | |
| 6,805,668 B1 | 10/2004 | Cadwell | |
| 6,819,956 B2 | 11/2004 | DiLorenzo | |
| 6,839,594 B2 | 1/2005 | Cohen | |
| 6,847,849 B2 | 1/2005 | Mamo | |
| 6,851,430 B2 | 2/2005 | Tsou | |
| 6,855,105 B2 | 2/2005 | Jackson, III | |
| 6,870,109 B1 | 3/2005 | Villarreal | |
| 6,901,928 B2 | 6/2005 | Loubser | |
| 6,902,569 B2 | 6/2005 | Parmer | |
| 6,916,294 B2 | 7/2005 | Ayad | |
| 6,916,330 B2 | 7/2005 | Simonson | |
| 6,926,728 B2 | 8/2005 | Zucherman | |
| 6,929,606 B2 | 8/2005 | Ritland | |
| 6,932,816 B2 | 8/2005 | Phan | |
| 6,945,933 B2 | 9/2005 | Branch | |
| 7,024,247 B2 | 4/2006 | Gliner | |
| 7,072,521 B1 | 7/2006 | Cadwell | |
| 7,079,883 B2 | 7/2006 | Marino | |
| 7,089,059 B1 | 8/2006 | Pless | |
| 7,104,965 B1 | 9/2006 | Jiang | |
| 7,129,836 B2 | 10/2006 | Lawson | |
| 7,153,279 B2 | 12/2006 | Ayad | |
| 7,156,686 B1 | 1/2007 | Sekela | |
| 7,177,677 B2 | 2/2007 | Kaula | |
| 7,214,197 B2 | 5/2007 | Prass | |
| 7,216,001 B2 | 5/2007 | Hacker | |
| 7,230,688 B1 | 6/2007 | Villarreal | |
| 7,236,822 B2 | 6/2007 | Dobak, III | |
| 7,258,688 B1 | 8/2007 | Shah | |
| 7,261,688 B2 | 8/2007 | Smith | |
| 7,294,127 B2 | 11/2007 | Leung | |
| 7,306,563 B2 | 12/2007 | Huang | |
| 7,310,546 B2 | 12/2007 | Prass | |
| 7,363,079 B1 | 4/2008 | Thacker | |
| 7,374,448 B1 | 5/2008 | Jepsen | |
| D574,955 S | 8/2008 | Lash | |
| 7,470,236 B1 | 12/2008 | Kelleher | |
| 7,496,407 B2 | 2/2009 | Odderson | |
| 7,522,953 B2 | 4/2009 | Kaula | |
| 7,546,993 B1 | 6/2009 | Walker | |
| 7,605,738 B2 | 10/2009 | Kuramochi | |
| 7,664,544 B2 | 2/2010 | Miles | |
| 7,689,292 B2 | 3/2010 | Hadzic | |
| 7,713,210 B2 | 5/2010 | Byrd | |
| D621,041 S | 8/2010 | Mao | |
| 7,775,974 B2 | 8/2010 | Buckner | |
| 7,789,695 B2 | 9/2010 | Radle | |
| 7,789,833 B2 | 9/2010 | Urbano | |
| 7,801,601 B2 | 9/2010 | Maschino | |
| 7,824,410 B2 | 11/2010 | Simonson | |
| 7,869,881 B2 | 1/2011 | Libbus | |
| 7,878,981 B2 | 2/2011 | Strother | |
| 7,914,350 B1 | 3/2011 | Bozich | |
| 7,963,927 B2 | 6/2011 | Kelleher | |
| 7,974,702 B1 | 7/2011 | Fain | |
| 7,983,761 B2 | 7/2011 | Giuntoli | |
| 7,987,001 B2 | 7/2011 | Teichman | |
| 7,988,688 B2 | 8/2011 | Webb | |
| 7,993,269 B2 | 8/2011 | Donofrio | |
| 8,002,770 B2 | 8/2011 | Swanson | |
| 8,061,014 B2 | 11/2011 | Smith | |
| 8,068,910 B2 | 11/2011 | Gerber | |
| 8,126,736 B2 | 2/2012 | Anderson | |
| 8,137,284 B2 | 3/2012 | Miles | |
| 8,147,421 B2 | 4/2012 | Farquhar | |
| 8,160,694 B2 | 4/2012 | Salmon | |
| 8,192,437 B2 | 6/2012 | Simonson | |
| 8,255,045 B2 | 8/2012 | Gharib | |
| 8,295,933 B2 | 10/2012 | Gerber | |
| D670,656 S | 11/2012 | Jepsen | |
| 8,311,791 B1 * | 11/2012 | Avisar | G09B 23/28 703/11 |
| 8,323,208 B2 * | 12/2012 | Davis | A61B 5/24 600/554 |
| 8,343,079 B2 | 1/2013 | Bartol | |
| 8,374,673 B2 | 2/2013 | Adcox | |
| RE44,049 E | 3/2013 | Herzon | |
| 8,419,758 B2 | 4/2013 | Smith | |
| 8,428,733 B2 | 4/2013 | Carlson | |
| 8,457,734 B2 | 6/2013 | Libbus | |
| 8,498,717 B2 | 7/2013 | Lee | |
| 8,515,520 B2 | 8/2013 | Brunnett | |
| 8,568,312 B2 | 10/2013 | Cusimano | |
| 8,568,317 B1 | 10/2013 | Gharib | |
| 8,594,779 B2 | 11/2013 | Denison | |
| 8,647,124 B2 * | 2/2014 | Bardsley | G09B 23/34 434/262 |
| 8,670,830 B2 | 3/2014 | Carlson | |
| 8,680,986 B2 | 3/2014 | Costantino | |
| 8,688,237 B2 | 4/2014 | Stanislaus | |
| 8,695,957 B2 | 4/2014 | Quintania | |
| 8,740,783 B2 | 6/2014 | Gharib | |
| 8,753,333 B2 | 6/2014 | Johnson | |
| 8,764,654 B2 | 7/2014 | Chmiel | |

(56) References Cited

U.S. PATENT DOCUMENTS

| | | |
|---|---|---|
| 8,805,527 B2 | 8/2014 | Mumford |
| 8,876,813 B2 | 11/2014 | Min |
| 8,886,280 B2 | 11/2014 | Kartush |
| 8,892,259 B2 | 11/2014 | Bartol |
| 8,926,509 B2 | 1/2015 | Magar |
| 8,942,797 B2 | 1/2015 | Bartol |
| 8,956,418 B2 | 2/2015 | Wasielewski |
| 8,958,869 B2 | 2/2015 | Kelleher |
| 8,971,983 B2 | 3/2015 | Gilmore |
| 8,986,301 B2 | 3/2015 | Wolf |
| 8,989,855 B2 | 3/2015 | Murphy |
| 9,031,658 B2 | 5/2015 | Chiao |
| 9,037,226 B2 | 5/2015 | Hacker |
| 9,078,671 B2 | 7/2015 | Beale |
| 9,084,550 B1 | 7/2015 | Bartol |
| 9,084,551 B2 | 7/2015 | Brunnett |
| 9,119,533 B2 | 9/2015 | Ghaffari |
| 9,121,423 B2 | 9/2015 | Sharpe |
| 9,149,188 B2 | 10/2015 | Eng |
| 9,155,503 B2 | 10/2015 | Cadwell |
| 9,204,830 B2 | 12/2015 | Zand |
| 9,247,952 B2 | 2/2016 | Bleich |
| 9,295,401 B2 | 3/2016 | Cadwell |
| 9,295,461 B2 | 3/2016 | Bojarski |
| 9,339,332 B2 | 5/2016 | Srivastava |
| 9,352,153 B2 | 5/2016 | Van Dijk |
| 9,370,654 B2 | 6/2016 | Scheiner |
| 9,579,503 B2 | 2/2017 | McKinney |
| 9,616,233 B2 | 4/2017 | Shi |
| 9,622,684 B2 | 4/2017 | Wybo |
| 9,714,350 B2 | 7/2017 | Hwang |
| 9,730,634 B2 | 8/2017 | Cadwell |
| 9,788,905 B2 * | 10/2017 | Avisar ................ G06F 3/04815 |
| 9,820,768 B2 | 11/2017 | Gee |
| 9,855,431 B2 | 1/2018 | Ternes |
| 9,913,594 B2 | 3/2018 | Li |
| 9,935,395 B1 | 4/2018 | Jepsen |
| 9,999,719 B2 | 6/2018 | Kitchen |
| 10,022,090 B2 | 7/2018 | Whitman |
| 10,039,461 B2 * | 8/2018 | Cadwell ................ A61B 5/296 |
| 10,039,915 B2 | 8/2018 | McFarlin |
| 10,092,349 B2 | 10/2018 | Engeberg |
| 10,154,792 B2 | 12/2018 | Sakai |
| 10,292,883 B2 | 5/2019 | Jepsen |
| 10,342,452 B2 | 7/2019 | Sterrantino |
| 10,349,862 B2 | 7/2019 | Sterrantino |
| 10,398,369 B2 | 9/2019 | Brown |
| 10,418,750 B2 | 9/2019 | Jepsen |
| 10,631,912 B2 | 4/2020 | McFarlin |
| 10,783,801 B1 * | 9/2020 | Beaubien ............ A61B 5/0245 |
| 11,189,379 B2 * | 11/2021 | Giataganas ............ G09B 9/00 |
| 2001/0031916 A1 | 10/2001 | Bennett |
| 2001/0039949 A1 | 11/2001 | Loubser |
| 2001/0049524 A1 | 12/2001 | Morgan |
| 2001/0056280 A1 | 12/2001 | Underwood |
| 2002/0001995 A1 | 1/2002 | Lin |
| 2002/0001996 A1 | 1/2002 | Seki |
| 2002/0007129 A1 | 1/2002 | Marino |
| 2002/0007188 A1 | 1/2002 | Arambula |
| 2002/0055295 A1 | 5/2002 | Itai |
| 2002/0065481 A1 | 5/2002 | Cory |
| 2002/0072686 A1 | 6/2002 | Hoey |
| 2002/0095080 A1 | 7/2002 | Cory |
| 2002/0149384 A1 | 10/2002 | Reasoner |
| 2002/0161415 A1 | 10/2002 | Cohen |
| 2002/0183647 A1 | 12/2002 | Gozani |
| 2002/0193779 A1 | 12/2002 | Yamazaki |
| 2002/0193843 A1 | 12/2002 | Hill |
| 2002/0194934 A1 | 12/2002 | Taylor |
| 2003/0032966 A1 | 2/2003 | Foley |
| 2003/0045808 A1 | 3/2003 | Kaula |
| 2003/0078618 A1 | 4/2003 | Fey |
| 2003/0088185 A1 * | 5/2003 | Prass ................ A61B 5/4893 |
| | | 600/546 |
| 2003/0105503 A1 | 6/2003 | Marino |
| 2003/0171747 A1 | 9/2003 | Kanehira |
| 2003/0199191 A1 | 10/2003 | Ward |
| 2003/0212335 A1 | 11/2003 | Huang |
| 2004/0019370 A1 | 1/2004 | Gliner |
| 2004/0034340 A1 | 2/2004 | Biscup |
| 2004/0068203 A1 | 4/2004 | Gellman |
| 2004/0135528 A1 | 7/2004 | Yasohara |
| 2004/0172114 A1 | 9/2004 | Hadzic |
| 2004/0199084 A1 | 10/2004 | Kelleher |
| 2004/0204628 A1 | 10/2004 | Rovegno |
| 2004/0225228 A1 | 11/2004 | Ferree |
| 2004/0229495 A1 | 11/2004 | Negishi |
| 2004/0230131 A1 | 11/2004 | Kassab |
| 2004/0260358 A1 | 12/2004 | Vaughan |
| 2005/0004593 A1 | 1/2005 | Simonson |
| 2005/0004623 A1 | 1/2005 | Miles |
| 2005/0075067 A1 | 4/2005 | Lawson |
| 2005/0075578 A1 | 4/2005 | Gharib |
| 2005/0080418 A1 | 4/2005 | Simonson |
| 2005/0085743 A1 * | 4/2005 | Hacker ................ A61B 5/24 |
| | | 600/554 |
| 2005/0119660 A1 | 6/2005 | Bourlion |
| 2005/0149143 A1 | 7/2005 | Libbus |
| 2005/0159659 A1 | 7/2005 | Sawan |
| 2005/0182454 A1 | 8/2005 | Gharib |
| 2005/0182456 A1 | 8/2005 | Ziobro |
| 2005/0215993 A1 | 9/2005 | Phan |
| 2005/0256582 A1 | 11/2005 | Ferree |
| 2005/0261559 A1 | 11/2005 | Mumford |
| 2006/0004424 A1 | 1/2006 | Loeb |
| 2006/0009754 A1 | 1/2006 | Boese |
| 2006/0025702 A1 | 2/2006 | Sterrantino |
| 2006/0025703 A1 | 2/2006 | Miles |
| 2006/0052828 A1 | 3/2006 | Kim |
| 2006/0069315 A1 | 3/2006 | Miles |
| 2006/0085048 A1 | 4/2006 | Cory |
| 2006/0085049 A1 | 4/2006 | Cory |
| 2006/0122514 A1 | 6/2006 | Byrd |
| 2006/0173383 A1 | 8/2006 | Esteve |
| 2006/0200023 A1 | 9/2006 | Melkent |
| 2006/0241725 A1 | 10/2006 | Libbus |
| 2006/0258951 A1 | 11/2006 | Bleich |
| 2006/0264777 A1 | 11/2006 | Drew |
| 2006/0276702 A1 | 12/2006 | McGinnis |
| 2006/0292919 A1 | 12/2006 | Kruss |
| 2007/0016097 A1 | 1/2007 | Farquhar |
| 2007/0021682 A1 | 1/2007 | Gharib |
| 2007/0032841 A1 | 2/2007 | Urmey |
| 2007/0049962 A1 | 3/2007 | Marino |
| 2007/0097719 A1 | 5/2007 | Parramon |
| 2007/0184422 A1 | 8/2007 | Takahashi |
| 2007/0270918 A1 | 11/2007 | De Bel |
| 2007/0282217 A1 | 12/2007 | McGinnis |
| 2008/0015612 A1 | 1/2008 | Urmey |
| 2008/0027507 A1 | 1/2008 | Bijelic |
| 2008/0039914 A1 | 2/2008 | Cory |
| 2008/0058606 A1 | 3/2008 | Miles |
| 2008/0064976 A1 | 3/2008 | Kelleher |
| 2008/0065144 A1 | 3/2008 | Marino |
| 2008/0065178 A1 | 3/2008 | Kelleher |
| 2008/0071191 A1 | 3/2008 | Kelleher |
| 2008/0077198 A1 | 3/2008 | Webb |
| 2008/0082136 A1 | 4/2008 | Gaudiani |
| 2008/0097164 A1 | 4/2008 | Miles |
| 2008/0167574 A1 | 7/2008 | Farquhar |
| 2008/0183190 A1 | 7/2008 | Adcox |
| 2008/0183915 A1 | 7/2008 | Iima |
| 2008/0194970 A1 | 8/2008 | Steers |
| 2008/0214903 A1 | 9/2008 | Orbach |
| 2008/0218393 A1 | 9/2008 | Kuramochi |
| 2008/0254672 A1 | 10/2008 | Dennes |
| 2008/0269777 A1 | 10/2008 | Appenrodt |
| 2008/0281313 A1 | 11/2008 | Fagin |
| 2008/0300650 A1 | 12/2008 | Gerber |
| 2008/0306348 A1 | 12/2008 | Kuo |
| 2009/0018399 A1 | 1/2009 | Martinelli |
| 2009/0088660 A1 | 4/2009 | McMorrow |
| 2009/0105604 A1 | 4/2009 | Bertagnoli |
| 2009/0143797 A1 | 6/2009 | Smith |

(56) References Cited

U.S. PATENT DOCUMENTS

| | | |
|---|---|---|
| 2009/0177112 A1 | 7/2009 | Gharib |
| 2009/0182322 A1 | 7/2009 | Frank |
| 2009/0197476 A1 | 8/2009 | Wallace |
| 2009/0204016 A1 | 8/2009 | Gharib |
| 2009/0209879 A1 | 8/2009 | Kaula |
| 2009/0221153 A1 | 9/2009 | Santangelo |
| 2009/0240117 A1 | 9/2009 | Chmiel |
| 2009/0259108 A1 | 10/2009 | Miles |
| 2009/0279767 A1 | 11/2009 | Kukuk |
| 2009/0281595 A1 | 11/2009 | King |
| 2009/0299439 A1 | 12/2009 | Mire |
| 2010/0004949 A1 | 1/2010 | O'Brien |
| 2010/0036280 A1 | 2/2010 | Ballegaard |
| 2010/0036384 A1 | 2/2010 | Gorek |
| 2010/0049188 A1 | 2/2010 | Nelson |
| 2010/0106011 A1 | 4/2010 | Byrd |
| 2010/0152604 A1 | 6/2010 | Kaula |
| 2010/0152811 A1 | 6/2010 | Flaherty |
| 2010/0152812 A1 | 6/2010 | Flaherty |
| 2010/0160731 A1 | 6/2010 | Giovannini |
| 2010/0168561 A1 | 7/2010 | Anderson |
| 2010/0191311 A1 | 7/2010 | Scheiner |
| 2010/0286554 A1 | 11/2010 | Davis |
| 2010/0317989 A1 | 12/2010 | Gharib |
| 2011/0004207 A1 | 1/2011 | Wallace |
| 2011/0028860 A1 | 2/2011 | Chenaux |
| 2011/0071418 A1 | 3/2011 | Stellar |
| 2011/0082383 A1 | 4/2011 | Cory |
| 2011/0160731 A1 | 6/2011 | Bleich |
| 2011/0184308 A1 | 7/2011 | Kaula |
| 2011/0230734 A1 | 9/2011 | Fain |
| 2011/0230782 A1 | 9/2011 | Bartol |
| 2011/0245647 A1 | 10/2011 | Stanislaus |
| 2011/0270120 A1 | 11/2011 | McFarlin |
| 2011/0270121 A1 | 11/2011 | Johnson |
| 2011/0295579 A1 | 12/2011 | Tang |
| 2011/0313530 A1 | 12/2011 | Gharib |
| 2012/0004516 A1 | 1/2012 | Eng |
| 2012/0071784 A1 | 3/2012 | Melkent |
| 2012/0109000 A1 | 5/2012 | Kaula |
| 2012/0109004 A1 | 5/2012 | Cadwell |
| 2012/0220891 A1 | 8/2012 | Kaula |
| 2012/0238893 A1 | 9/2012 | Farquhar |
| 2012/0245439 A1 | 9/2012 | Andre |
| 2012/0277780 A1 | 11/2012 | Smith |
| 2012/0296230 A1 | 11/2012 | Davis |
| 2013/0027186 A1 | 1/2013 | Cinbis |
| 2013/0030257 A1 | 1/2013 | Nakata |
| 2013/0090641 A1 | 4/2013 | McKinney |
| 2013/0245722 A1 | 9/2013 | Ternes |
| 2013/0261422 A1 | 10/2013 | Gilmore |
| 2013/0267874 A1 | 10/2013 | Marcotte |
| 2014/0058284 A1 | 2/2014 | Bartol |
| 2014/0073985 A1 | 3/2014 | Sakai |
| 2014/0074084 A1 | 3/2014 | Engeberg |
| 2014/0088463 A1 | 3/2014 | Wolf |
| 2014/0121555 A1 | 5/2014 | Scott |
| 2014/0275914 A1 | 9/2014 | Li |
| 2014/0275926 A1 | 9/2014 | Scott |
| 2014/0288389 A1 | 9/2014 | Gharib |
| 2014/0303452 A1 | 10/2014 | Ghaffari |
| 2015/0012066 A1 | 1/2015 | Underwood |
| 2015/0088029 A1 | 3/2015 | Wybo |
| 2015/0088030 A1 | 3/2015 | Taylor |
| 2015/0112325 A1 | 4/2015 | Whitman |
| 2015/0202395 A1 | 7/2015 | Fromentin |
| 2015/0238260 A1 | 8/2015 | Nau, Jr. |
| 2015/0250423 A1 | 9/2015 | Hacker |
| 2015/0311607 A1 | 10/2015 | Ding |
| 2015/0380511 A1 | 12/2015 | Irsigler |
| 2016/0000382 A1 | 1/2016 | Jain |
| 2016/0015299 A1 | 1/2016 | Chan |
| 2016/0038072 A1 | 2/2016 | Brown |
| 2016/0038073 A1 | 2/2016 | Brown |
| 2016/0038074 A1 | 2/2016 | Brown |
| 2016/0135834 A1 | 5/2016 | Bleich |
| 2016/0174861 A1 | 6/2016 | Cadwell |
| 2016/0199659 A1 | 7/2016 | Jiang |
| 2016/0235999 A1 | 8/2016 | Nuta |
| 2016/0262699 A1 | 9/2016 | Goldstone |
| 2016/0270679 A1 | 9/2016 | Mahon |
| 2016/0287112 A1 | 10/2016 | McFarlin |
| 2016/0287861 A1 | 10/2016 | McFarlin |
| 2016/0317053 A1 | 11/2016 | Srivastava |
| 2016/0339241 A1 | 11/2016 | Hargrove |
| 2017/0056643 A1 | 3/2017 | Herb |
| 2017/0231508 A1 | 8/2017 | Edwards |
| 2017/0273592 A1 | 9/2017 | Sterrantino |
| 2018/0345004 A1 | 12/2018 | McFarlin |
| 2019/0180637 A1* | 6/2019 | Mealer .............. G06F 3/014 |
| 2019/0350485 A1 | 11/2019 | Sterrantino |

FOREIGN PATENT DOCUMENTS

| | | |
|---|---|---|
| AU | 607977 B2 | 3/1991 |
| AU | 2005269287 A1 | 2/2006 |
| AU | 2006217448 A1 | 8/2006 |
| AU | 2003232111 B2 | 10/2008 |
| AU | 2004263152 B2 | 8/2009 |
| AU | 2005269287 B2 | 5/2011 |
| AU | 2008236665 B2 | 8/2013 |
| AU | 2012318436 A1 | 4/2014 |
| AU | 2016244152 A1 | 11/2017 |
| AU | 2016244152 B2 | 12/2018 |
| AU | 2019201702 A1 | 4/2019 |
| BR | 9604655 C1 | 12/1999 |
| BR | 0609144 A2 | 2/2010 |
| CA | 2144211 C | 5/2005 |
| CA | 2229391 C | 9/2005 |
| CA | 2574845 A1 | 2/2006 |
| CA | 2551185 C | 10/2007 |
| CA | 2662474 A1 | 3/2008 |
| CA | 2850784 A1 | 4/2013 |
| CA | 2769658 C | 1/2016 |
| CA | 2981635 A1 | 10/2016 |
| CN | 101018585 A | 8/2007 |
| CN | 100571811 C | 12/2009 |
| CN | 104066396 A | 9/2014 |
| CN | 103052424 B | 12/2015 |
| CN | 104080509 B | 9/2017 |
| CN | 104717996 B | 1/2018 |
| CN | 107666939 A | 2/2018 |
| CN | 111419179 A | 7/2020 |
| DE | 2753109 A1 | 6/1979 |
| DE | 8803153 U1 | 6/1988 |
| DE | 3821219 C1 | 8/1989 |
| DE | 29510204 U1 | 8/1995 |
| DE | 19530869 A1 | 2/1997 |
| DE | 29908259 U1 | 7/1999 |
| DE | 19921279 C1 | 11/2000 |
| DE | 19618945 C2 | 2/2003 |
| EP | 0161895 A2 | 11/1985 |
| EP | 298268 | 1/1989 |
| EP | 0719113 A1 | 7/1996 |
| EP | 0759307 A2 | 2/1997 |
| EP | 0836514 A2 | 4/1998 |
| EP | 890341 | 1/1999 |
| EP | 972538 | 1/2000 |
| EP | 1656883 A1 | 5/2006 |
| EP | 1115338 B1 | 8/2006 |
| EP | 1804911 A1 | 7/2007 |
| EP | 1534130 A4 | 9/2008 |
| EP | 1804911 B1 | 1/2012 |
| EP | 2481338 A3 | 9/2012 |
| EP | 2763616 A1 | 8/2014 |
| EP | 1385417 B1 | 4/2016 |
| EP | 1680177 B1 | 4/2017 |
| EP | 3277366 A1 | 2/2018 |
| ES | 2725489 T3 | 9/2019 |
| FI | 73878 C | 12/1987 |
| FR | 2624373 A1 | 6/1989 |
| FR | 2624748 B1 | 10/1995 |
| FR | 2796846 A1 | 2/2001 |
| FR | 2795624 B1 | 9/2001 |

(56) References Cited

FOREIGN PATENT DOCUMENTS

| | | |
|---|---|---|
| FR | 2835732 B1 | 11/2004 |
| GB | 1534162 A | 11/1978 |
| GB | 2049431 A | 12/1980 |
| GB | 2052994 A | 2/1981 |
| GB | 2452158 A | 2/2009 |
| GB | 2519302 B | 4/2016 |
| IT | 1221615 B | 7/1990 |
| JP | H0723964 A | 1/1995 |
| JP | 2000028717 A | 1/2000 |
| JP | 3188437 B2 | 7/2001 |
| JP | 2003524452 A | 8/2003 |
| JP | 2004522497 A | 7/2004 |
| JP | 2008508049 A | 3/2008 |
| JP | 4295086 B2 | 7/2009 |
| JP | 4773377 B2 | 9/2011 |
| JP | 4854900 B2 | 1/2012 |
| JP | 4987709 B2 | 7/2012 |
| JP | 5132310 B2 | 1/2013 |
| JP | 2014117328 A | 6/2014 |
| JP | 2014533135 A | 12/2014 |
| JP | 6145916 B2 | 6/2017 |
| JP | 2018514258 A | 6/2018 |
| JP | 2018514258 A5 | 5/2019 |
| JP | 6749338 B2 | 9/2020 |
| KR | 100632980 B1 | 10/2006 |
| KR | 1020070106675 A | 11/2007 |
| KR | 100877229 B1 | 1/2009 |
| KR | 20140074973 A | 6/2014 |
| KR | 1020170133499 A | 12/2017 |
| KR | 102092583 B1 | 3/2020 |
| KR | 1020200033979 A | 3/2020 |
| NZ | 541889 A | 4/2010 |
| SE | 467561 B | 8/1992 |
| SE | 508357 C2 | 9/1998 |
| WO | 1999037359 A1 | 7/1999 |
| WO | 2000038574 A1 | 7/2000 |
| WO | 2000066217 A1 | 11/2000 |
| WO | 2001037728 A1 | 5/2001 |
| WO | 2001078831 A2 | 10/2001 |
| WO | 2001087154 A1 | 11/2001 |
| WO | 2001093748 A2 | 12/2001 |
| WO | 2002082982 A1 | 10/2002 |
| WO | 2003005887 A2 | 1/2003 |
| WO | 2003034922 A1 | 5/2003 |
| WO | 2003094744 A1 | 11/2003 |
| WO | 2004064632 A1 | 8/2004 |
| WO | 2005030318 A1 | 4/2005 |
| WO | 2006015069 A1 | 2/2006 |
| WO | 2006026482 A2 | 3/2006 |
| WO | 2006042241 A2 | 4/2006 |
| WO | 2006113394 A2 | 10/2006 |
| WO | 2008002917 A2 | 1/2008 |
| WO | 2008005843 A2 | 1/2008 |
| WO | 2008097407 A2 | 8/2008 |
| WO | 2009051965 A1 | 4/2009 |
| WO | 2010090835 A1 | 8/2010 |
| WO | 2011014598 A1 | 2/2011 |
| WO | 2011150502 A2 | 12/2011 |
| WO | 2013019757 A2 | 2/2013 |
| WO | 2013052815 A1 | 4/2013 |
| WO | 2013151770 A1 | 10/2013 |
| WO | 2015069962 A1 | 5/2015 |
| WO | 2016160477 A1 | 10/2016 |

OTHER PUBLICATIONS

Ott, "Noise Reduction Techniques in Electronic Systems" Second Edition; John Wiley & Sons, p. 62, 1988.
Stecker et al. "Strategies for minimizing 60 Hz pickup during evoked potential recording", Electroencephalography and clinical Neurophysiology 100 (1996) 370-373.
Wood et al. "Comparative analysis of power-line interference between two- or three-electrode biopotential amplifiers" Biomedical Engineering, Med. & Biol. Eng. & Comput., 1995, 33, 63-68.
Clements, et al., "Evoked and Spontaneous Electromyography to Evaluate Lumbosacral Pedicle Screw Placement", 21 (5):600-604 (1996).
Danesh-Clough, et al., "The Use of Evoked EMG in Detecting Misplaced Thoracolumbar Pedicle Screws", 26(12):1313-1316 (2001).
Dezawa et al., "Retroperitoneal Laparoscopic Lateral Approach to the Lumbar Spine: A New Approach, Technique, and Clinical Trial", Journal of Spinal Disorders 13(2):138-143 (2000).
Epstein, et al., "Evaluation of Intraoperative Somatosensory-Evoked Potential Monitoring During 100 Cervical Operations", 18(6):737-747 (1993), J.B. Lippincott Company.
Goldstein, et al., "Minimally Invasive Endoscopic Surgery of the Lumbar Spine", Operative Techniques in Orthopaedics, 7 (1):27-35 (1997).
Greenblatt, et al., "Needle Nerve Stimulator-Locator", 41 (5):599-602 (1962).
H.M. Mayer, "Minimally Invasive Spine Surgery, A Surgical Manual", Chapter 12, pp. 117-131 (2000).
Hinrichs, et al., "A trend-detection algorithm for intraoperative EEG monitoring", Med. Eng. Phys. 18 (8):626-631 (1996).
Bergey et al., "Endoscopic Lateral Transpsoas Approach to the Lumbar Spine", Spine 29 (15):1681-1688 (2004).
Holland, "Spine Update, Intraoperative Electromyography During Thoracolumbar Spinal Surgery", 23 (17):1915-1922 (1998).
Hovey, A Guide to Motor Nerve Monitoring, pp. Mar. 1-31, 20, 1998, The Magstim Company Limited.
Kevin T. Foley, et al., "Microendoscipic Discectomy" Techniques in Neurosurgery, 3:(4):301-307, © 1997 Lippincott-Raven Publishers, Philadelphia.
Kossmann et al., "The use of a retractor system (SynFrame) for open, minimal invasive reconstruction of the anterior column of the thoracic and lumbar spine", 10:396-402 (2001).
Kossmann, et al., "Minimally Invasive Vertebral Replacement with Cages in Thoracic and Lumbar Spine", European Journal of Trauma, 2001, No. 6, pp. 292-300.
Lenke, et al., "Triggered Electromyographic Threshold for Accuracy of Pedicle Screw Placement, An Animal Model and Clinical Correlation", 20 (14):1585-1591 (1995).
Lomanto et al., "7th World Congress of Endoscopic Surgery" Singapore, Jun. 1-4, 2000 Monduzzi Editore S.p.A.; email: monduzzi@monduzzi.com, pp. 97-103 and 105-111.
Maguire, et al., "Evaluation of Intrapedicular Screw Position Using Intraoperative Evoked Electromyography", 20 (9):1068-1074 (1995).
Mathews et al., "Laparoscopic Discectomy With Anterior Lumbar Interbody Fusion, A Preliminary Review", 20 (16):1797-1802, (1995), Lippincott-Raven Publishers.
Bertagnoli, et al., "The AnteroLateral transPsoatic Approach (ALPA), A New Technique for Implanting Prosthetic Disc-Nucleus Devices", 16 (4):398-404 (2003).
Michael R. Isley, et al., "Recent Advances in Intraoperative Neuromonitoring of Spinal Cord Function: Pedicle Screw Stimulation Techniques", Am. J. End TechnoL 37:93-126 (1997).
Minahan, et al., "The Effect of Neuromuscular Blockade on Pedicle Screw Stimulation Thresholds" 25(19):2526-2530 (2000).
Pimenta et al., "Implante de prótese de núcleo pulposo: análise inicial", J Bras Neurocirurg 12 (2):93-96, (2001).
Raymond J. Gardocki, MD, "Tubular diskectomy minimizes collateral damage", AAOS Now, Sep. 2009 Issue, http://www.aaos.org/news/aaosnow/sep09/clinical12.asp.
Reidy, et al., "Evaluation of electromyographic monitoring during insertion of thoracic pedicle screws", British Editorial Society of Bone and Joint Surgery 83 (7):1009-1014, (2001).
Rose et al., "Persistently Electrified Pedicle Stimulation Instruments in Spinal Instrumentation: Technique and Protocol Development", Spine: 22(3): 334-343 (1997).
Teresa Riordan "Patents; A businessman invents a device to give laparoscopic surgeons a better view of their worK", New York Times www.nytimes.com/2004/29/business/patents-businessman-invents-device-give-la (Mar. 2004).
Toleikis, et al., "The usefulness of Electrical Stimulation for Assessing Pedicle Screw Placements", Journal of Spinal Disorders, 13 (4):283-289 (2000).

(56) References Cited

OTHER PUBLICATIONS

U.Schick, et al., "Microendoscopic lumbar discectomy versus open surgery: an intraoperative EMG study", pp. 20-26, Published online: Jul. 31, 2001 © Springer-Verlag 2001.

Bose, et al., "Neurophysiologic Monitoring of Spinal Nerve Root Function During Instrumented Posterior Lumbar Spine Surgery", 27 (13):1440-1450 (2002).

Vaccaro, et al., "Principles and Practice of Spine Surgery", Mosby, Inc. ©2003, Chapter 21, pp. 275-281.

Vincent C. Traynelis, "Spinal arthroplasty", Neurosurg Focus 13 (2):1-7. Article 10, (2002).

Welch, et al., "Evaluation with evoked and spontaneous electromyography during lumbar instrumentation: a prospective study", J Neurosurg 87:397-402, (1997).

Zouridakis, et al., "A Concise Guide to Intraoperative Monitoring", Library of Congress card No. 00-046750, Chapters, p. 21, chapter 4, p. 58 and chapter 7 pp. 119-120.

Medtronic, "Nerve Integrity Monitor, Intraoperative EMG Monitor, User's Guide", Medtronic Xomed U.K. Ltd., Unit 5, West Point Row, Great Park Road, Almondsbury, Bristol B5324QG, England, pp. 1-39.

Chapter 9, "Root Finding and Nonlinear Sets of Equations", Chapter 9:350-354, http://www.nr.com.

Digitimer Ltd., 37 Hydeway, Welwyn Garden City, Hertfordshire. AL7 3BE England, email:sales@digitimer.com, website: www.digitimer.com, "Constant Current High Voltage Stimulator, Model DS7A, For Percutaneous Stimulation of Nerve and Muscle Tissue".

Deletis et al., "The role of intraoperative neurophysiology in the protection or documentation of surgically induced injury to the spinal cord", Correspondence Address: Hyman Newman Institute for Neurology & Neurosurgery, Beth Israel Medical Center, 170 East End Ave., Room 311, NY 10128.

Butterworth et al., "Effects of Halothane and Enflurane on Firing Threshold of Frog Myelinated Axon", Journal of Physiology 411:493-516, (1989) From the Anesthesia Research Labs, Brigham and Women's Hospital, Harvard Medical School, 75 Francis St., Boston, MA 02115, jp.physoc.org.

Calancie, et al., "Threshold-level multipulse transcranial electrical stimulation of motor cortex for intraoperative monitoring of spinal motor tracts: description of method and comparison to somatosensory evoked potential monitoring" J Neurosurg 88:457-470 (1998).

Calancie, et al., "Threshold-level repetitive transcranial electrical stimulation for intraoperative monitoring of central motor conduction", J. Neurosurg 95:161-168 (2001).

Calancie, et al., Stimulus-Evoked EMG Monitoring During Transpedicular Lumbosacral Spine Instrumentation, Initial Clinical Results, 19 (24):2780-2786 (1994).

Carl T. Brighton, "Clinical Orthopaedics and Related Research", Clinical Orthopaedics and related research No. 384, pp. 82-100 (2001).

Aage R. Møller, "Intraoperative Neurophysiologic Monitoring", University of Pittsburgh, School of Medicine Pennsylvania, © 1995 by Harwood Academic Publishers GmbH.

Urmey "Using the nerve stimulator for peripheral or plexus nerve blocks" Minerva Anesthesiology 2006; 72:467-71.

Review of section 510(k) premarket notification for "K013215: NuVasive NeuroVision JJB System", Department of Health and Human Services, FDA, Oct. 16, 2001.

\* cited by examiner

Patient Simulator Controls — 901

| Anesthesia | Technical Setup | Trace Characteristics | Pedicle Screw | Scripts |

Click on the spine to populate grids with pedicle screw sites. Click and drag slider to set pedicle screw integrity for each site. Set stimulation location to simulate pedicle screw stimulation in TEMG and Threshold modes. The stimulator output must be set to Probe 1 in procedure setup Channel Outputs as well as the mode's stimulus output.

Pedicle Stim — 906
Output: Probe 1
Stim Location: Right L4
Region: All Regions

Anatomical Spine
— 902
— 904

Pedicle Screw Locations — 909

| Location | Pedicle Screw Integrity — 908 | |
|---|---|---|
| ▽ Left Pedicle Sites — 910 | | |
| Left L2 | Low | High |
| Left L3 | Low | High |
| Left L4 | Low | High |
| ▽ Right Pedicle Sites — 912 | | |
| Right L2 | Low | High |
| Right L3 | Low | High |
| Right L4 | Low — 907 | High |

Owner: Admin, CadLink          Disclaimer

NEUROPHYSIOLOGICAL MONITORING TRAINING SIMULATOR

CROSS-REFERENCE

The present application relies on U.S. Patent Provisional Application No. 62/692,539, entitled "Intraoperative Neurophysiological Monitoring (IONM) Training Simulator" and filed on Jun. 29, 2018, for priority, which is herein incorporated by reference in its entirety.

FIELD

The present specification is related generally to the field of neurophysiological stimulation. More specifically, the present specification is related to a software-based medical training simulator for neurodiagnostic testing and IONM.

BACKGROUND

Intraoperative neurophysiological monitoring (IONM) is directed towards identifying, mapping and monitoring neural structures in accordance with their functions with a goal of preserving the structural integrity of these neural structures during physically invasive procedures such as surgery.

Conventionally, trainees learning to operate neurodiagnostic and IONM systems rely on didactic training and images or videos captured from previously recorded patient cases, observing/shadowing experienced users in a clinical environment, and working under supervision in a clinical environment. Often a trainee may not experience a certain event, either technical, anesthetic or surgical, until it happens with a patient in a real clinical environment. Hence, the trainees currently are required to spend significant amounts of time in a clinical environment to gain exposure to real events as some events may occur infrequently in the real world.

Currently, there are some training simulators available in the market for providing training to neurodiagnostic and IONM trainees. Simulation is a powerful tool for learning about rare patient events, and about common technical and operational problems, as well as how to run an IONM instrument and perform monitoring effectively. Users requiring training include both technical and medically-trained professionals.

However, these training simulators requires the use of hardware including their own IONM devices. The simulators can simulate plug-in errors, but cannot simulate the effects of anesthesia, positioning, temperature, interference from other devices, surgical events and/or comorbidities. Currently available IONM training simulators do not simulate realistic waveforms in their software applications and do not simulate the effect of likely events encountered in a clinical environment on recorded waveforms.

For example, latency shifts and amplitude changes in a patient's monitoring data may be caused by environmental factors (and not surgery), such as limb positioning, temperature, and other machines hooked to a patient. Such environmental factors interfere with the currently available simulator's ability to accurately simulate patient data.

FIG. 1A illustrates a pictorial depiction of stimulus provided to a theoretical patient and corresponding response waveforms recorded in a conventional IONM system. In a conventional IONM system stimulator, when a stimulus 102 is provided to a theoretical patient 104, neurological response collected via an electrode 106 is displayed as waveforms on a display instrument 108 of an IONM system.

FIG. 1B illustrates a conventional simulator of an IONM system. As shown in FIG. 1B, the patient 104 is replaced by a simulator 110 which provides a response on being triggered with an input stimulus 112, which is displayed as synthesized (canned) waveforms on the display instrument 108. Conventionally, a pre-defined response is mixed with random noise and is fed back to the instrument 108. The underlying response is found by averaging and filtering for teaching the trainees how to use the instrument. However, the response on the instrument 108 does not simulate an actual patient, as the responses are 'canned' or pre-recorded and only a small number of responses are made available to illustrate features of the recording instrument 108.

However, when a real patient is being monitored via an IONM system, a multitude of input signals are received by stimulus generation body sites, such as the patient's brain, and corresponding response waveforms are generated. FIG. 2 illustrates a real person being monitored via an IONM system. A plurality of stimulus 202 from sources such as, but not limited to, electrode noise, anesthesia effects, electroencephalogram (EEG) signals, muscle signals, other noise sources and other stimulating signals are received by a patient 204, which causes the patient's brain to produce a plurality of stochastic responses 206 which are captured by an electrode 208 of the IONM system for processing and display as a waveform on instrument 210.

It is not possible to simulate the receiving and processing of the multitude of input stimulus 202 to produce a synthesized waveform for display, because such processing is an n-factorial problem. The number of cases needed to represent combinations of all input stimuli parameters is unmanageable and a significant computational power is needed to simulate highly connected systems.

The net computational load in IONM simulation systems may involve a few hundred extensive calculations for each input stimulus. In conventional simulation, a hardware device creates a trigger and measures the response. This paradigm forces high bandwidth, time critical computation at precise times. The usual implementation has a "hard wired" trigger line with various low latency switching elements to select one or more input stimulation devices. The stimulation devices, once triggered, do not have zero response time and the actual delay is subtracted from the response to correct for this error. In addition, when multiple stimuli need to be coordinated, the synchronization of the various input stimulation devices is problematic. Typically, a central processing unit is used to control all the input stimuli, stimuli timing, and stimuli intensities and then correct for all the errors therein. The tight timing and added computations when a trigger occurs requires even higher peak computational power, and most computer operating systems are not 'real time' and do not respond to synchronous inputs with synchronous outputs, making such processing difficult.

Hence, there is need for a software-based medical training simulator for neurodiagnostic testing and IONM which does not require connection to any neurodiagnostic or IONM hardware, thereby reducing the barrier to access for training centers and individuals. There is also need for a training simulator that provides simulations of a wide range of technical, anesthetic and surgical events likely to be encountered during typical use of the simulator.

SUMMARY

The present specification discloses a system for simulating a patient's physiological responses to one or more stimuli over a simulation timeframe, wherein the system comprises programmatic instructions stored in a tangible, non-transitory computer readable medium, wherein the programmatic instructions define a plurality of channels, each of said channels being virtually representative of an anatomical site of the patient, and wherein, when executed, the programmatic instructions: identify at least one of the plurality of channels as a stimulation site; identify a first subset of the plurality of channels as reference sites; generate simulation data indicative of the physiological responses at each channel in the first subset using predefined relationships between the plurality of channels and based on the one or more simulated stimuli; identify a second subset of the plurality of channels from the first subset, wherein each of the channels in the second subset has simulation data indicative of a physiological response that exceeds one or more pre-defined thresholds; generate data indicative of physiological responses at each channel in the second subset by: during each of a time window of a plurality of time windows within the simulation timeframe and for each channel in the second subset, identifying one or more signals that are expected to affect said channel at a future time T1; prior to future time T1 and for each channel in the second subset, generating data indicative of physiological responses which would result from the one or more signals that are expected to affect said channel at the future time T1; and associating the generated data with a time T2; receive a request for data corresponding to one or more of the time windows encompassing time T2; acquire the generated data associated with time T2 from each channel; and generate a data stream from each channel, wherein each data stream comprises the generated data associated with time T2.

Optionally, the stimulation site is a location where the one or more stimuli is to be virtually applied to the patient. Optionally, the one or more stimuli is at least one of an electrical stimulation, an auditory stimulation, or a visual stimulation.

Optionally, the reference sites are locations where physiological responses to the one or more simulated stimuli are to be determined.

Optionally, when executed, the programmatic instructions identify, from the first subset, a third subset of the plurality of channels, wherein each of the channels in the third subset has simulation data indicative of a physiological response that does not exceed one or more pre-defined thresholds. Optionally, when executed, the programmatic instructions do not generate a data stream from each channel in the third subset.

Optionally, a number of channels in the second subset is less than a number of channels in the first subset.

Optionally, the one or more signals that are expected to affect said channel at a future time T1 are a function of the one or more simulated stimuli, a simulated injury to the patient, at least one simulated physiological response occurring at another channel prior to time T1, are defined by at least one waveform having an amplitude exceeding a predefined threshold, are a function of simulated interference from an electrosurgical instrument, a simulated positioning of a portion of the patient's body, or simulated mains interference. Optionally, the one or more signals that are expected to affect said channel at a future time T1 are defined by at least one waveform originating from another channel having a virtual distance exceeding a predefined threshold, a simulation electrocardiogram (EKG) signal, a simulated motion artifact signal, or a simulated electromyography (EMG) signal. Optionally, when executed, the programmatic instructions further generate data indicative of physiological responses at each channel in the second subset by: during each time window within the simulation timeframe and for each channel in the second subset, identifying one or more global modulators that are expected to affect all channels in the second subset at a future time T1; and prior to time T1 and for each channel in the second subset, generating data indicative of physiological responses which would result from the global modulators that are expected to affect all channels in the second subset at future time T1. Optionally, the one or more global modulators that are expected to affect all channels in the second set at a future time T1 comprise a simulated temperature of the patient or a virtual administration of anesthesia to the patient.

Optionally, the time window is less than 1 second.

Optionally, when executed, the programmatic instructions further generate data indicative of physiological responses at each channel in the second subset by: during a second time window within the simulation timeframe and for each channel in the second subset, identifying a second set of one or more signals that are expected to affect said channel at a future time T3, wherein the second set of one or more signals are a function of at least some of the generated data associated with a time T2; prior to future time T3 and for each channel in the second subset, generating data indicative of physiological responses which would result from the second set of one or more signals; and associating the generated data with a time T4. Optionally, when executed, the programmatic instructions further receive a request for data corresponding to one or more of the time windows encompassing time T4; acquire the generated data associated with time T4 from each channel; and generate a data stream from each channel, wherein each data stream comprises the generated data associated with time T4.

The present specification also discloses a method for simulating a patient's physiological responses to one or more stimuli over a simulation timeframe, wherein the method comprises providing a simulation system that comprises programmatic instructions stored in a tangible, non-transitory computer readable medium, wherein the programmatic instructions define a plurality of channels, each of said channels being virtually representative of an anatomical site of the patient, and wherein, when executed, the programmatic instructions are configured to perform a simulation, the method comprising the steps of: identifying at least one of the plurality of channels as a stimulation site; identifying a first subset of the plurality of channels as reference sites; generating simulation data indicative of the physiological responses at each channel in the first subset using predefined relationships between the plurality of channels and based on the one or more simulated stimuli; identifying a second subset of the plurality of channels from the first subset, wherein each of the channels in the second subset has simulation data indicative of a physiological response that exceeds one or more predefined thresholds; generating data indicative of physiological responses at each channel in the second subset by: during each of a time window of a plurality of time windows within the simulation timeframe and for each channel in the second subset, identifying one or more signals that are expected to affect said channel at a future time T1; prior to future time T1 and for each channel in the second subset, generating data indicative of physiological responses which would result from the one or more signals that are expected to affect said channel at the future time T1; and associating the generated data with a time T2; receiving a request for data corresponding to one or more of the time windows encompassing time T2; acquiring the generated data associated with time T2 from each channel;

and generating a data stream from each channel, wherein each data stream comprises the generated data associated with time T2.

Optionally, the stimulation site is a location where the one or more stimuli is to be virtually applied to the patient. Optionally, the one or more stimuli is at least one of an electrical stimulation, an auditory stimulation, or a visual stimulation.

Optionally, the reference sites are locations where physiological responses to the one or more simulated stimuli are to be determined.

Optionally, the method further comprises identifying, from the first subset, a third subset of the plurality of channels, wherein each of the channels in the third subset has simulation data indicative of a physiological response that does not exceed one or more predefined thresholds. Optionally, the method further comprises not generating a data stream from each channel in the third subset.

Optionally, a number of channels in the second subset is less than a number of channels in the first subset.

Optionally, the one or more signals that are expected to affect said channel at a future time T1 are a function of the one or more simulated stimuli, a simulated injury to the patient, at least one simulated physiological response occurring at another channel prior to time T1, are defined by at least one waveform having an amplitude exceeding a predefined threshold, are a function of simulated interference from an electrosurgical instrument, a simulated positioning of a portion of the patient's body, or simulated mains interference. Optionally, the one or more signals that are expected to affect said channel at a future time T1 are defined by at least one waveform originating from another channel having a virtual distance exceeding a predefined threshold, a simulation electrocardiogram (EKG) signal, a simulated motion artifact signal, or a simulated electromyography (EMG) signal.

Optionally, the method further comprises generating data indicative of physiological responses at each channel in the second subset by: during each time window within the simulation timeframe and for each channel in the second subset, identifying one or more global modulators that are expected to affect all channels in the second subset at a future time T1; and prior to time T1 and for each channel in the second subset, generating data indicative of physiological responses which would result from the global modulators that are expected to affect all channels in the second subset at future time T1. Optionally, the one or more global modulators that are expected to affect all channels in the second set at a future time T1 comprise a simulated temperature of the patient or a virtual administration of anesthesia to the patient.

Optionally, the time window is less than 1 second.

Optionally, the method further comprises generating data indicative of physiological responses at each channel in the second subset by: during a second time window within the simulation timeframe and for each channel in the second subset, identifying a second set of one or more signals that are expected to affect said channel at a future time T3, wherein the second set of one or more signals are a function of at least some of the generated data associated with a time T2; prior to future time T3 and for each channel in the second subset, generating data indicative of physiological responses which would result from the second set of one or more signals; and associating the generated data with a time T4. Optionally, the method further comprises receiving a request for data corresponding to one or more of the time windows encompassing time T4; acquiring the generated data associated with time T4 from each channel; and generating a data stream from each channel, wherein each data stream comprises the generated data associated with time T4.

The present specification also discloses a method for providing a training simulator for IONM systems, the method comprising: receiving multiple stimulation inputs from a plurality of input stimulation pick up sites on a patient body; pruning the received input stimulations to determine the signals that require processing; scheduling the pruned stimulations for processing; and processing the scheduled stimulations to obtain a response corresponding to each stimulation pick up site.

Optionally, the method further comprises determining a plurality of input stimulus generation sites on the patient body and generating input stimulations.

Optionally, the method further comprises determining a plurality of stimulus pick up sites on the patient body.

The response may comprise waveforms being displayed on a display instrument of the IONM system, the waveforms depicting simulated patient response corresponding to the stimulation inputs.

Optionally, a number of pruned stimulations is less than a number of received stimulations from the plurality of stimulation pick up sites on the patient body.

Optionally, pruning the received input stimulations comprises ignoring the received stimulations generated at a site farther than a predefined threshold distance from a corresponding pick up site on the patient body.

Optionally, pruning the received input stimulations comprises ignoring the received stimulations that are smaller than a predefined threshold amplitude.

Optionally, scheduling the pruned stimulations comprises adding a time stamp to each of the pruned stimulations based on a nature of each stimulation. The scheduled stimulations may be processed serially based upon a corresponding time stamp. The response corresponding to a stimulation pick up site may be a weighted sum of all stimulations detectable at the site.

The aforementioned and other embodiments of the present shall be described in greater depth in the drawings and detailed description provided below.

BRIEF DESCRIPTION OF THE DRAWINGS

These and other features and advantages of the present specification will be further appreciated, as they become better understood by reference to the following detailed description when considered in connection with the accompanying drawings:

FIG. 9 illustrates an exemplary user interface for simulating pedicle screw stimulation with varying levels of pedicle screw integrity on a patient undergoing IONM, in accordance with an embodiment of the present specification.

DETAILED DESCRIPTION

Figure 1A:
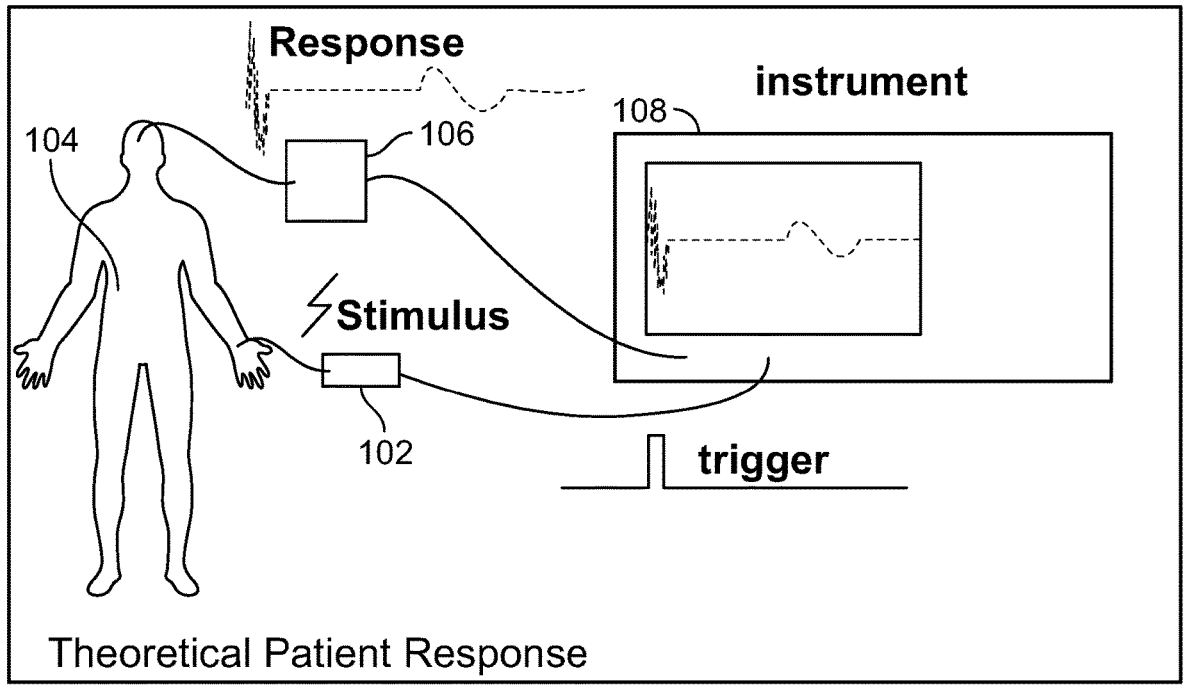
FIG. 1A illustrates a pictorial depiction of stimulus provided to a theoretical patient and corresponding response waveforms recorded in a conventional IONM system.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

In the description and claims of the application, each of the words "comprise" "include" and "have", and forms thereof, are not necessarily limited to members in a list with which the words may be associated. It should be noted herein that any feature or component described in association with a specific embodiment may be used and implemented with any other embodiment unless clearly indicated otherwise.

As used herein, the indefinite articles "a" and "an" mean "at least one" or "one or more" unless the context clearly dictates otherwise.

The term "intraoperative neurophysiological monitoring" or "IONM" refers to systems and methods of stimulating and recording various pathways throughout the nervous system during surgery to reduce the risks of neurological deficits.

The term "anesthesia agent" refers to inhalational and/or intravenously administered chemical compositions that are used to induce and maintain a patient in a sleep-like state during surgery and can affect the patient's physiological response to stimulation and recording during IONM.

The term "electrosurgery interference" refers to electrical signals, generated by electrosurgery devices used during surgery to help prevent blood loss, that interfere with recorded patient signals during IONM.

The term "mains interference" refers to the frequency associated with mains electricity, typically 50-60 Hz, that can interfere with recorded signals during IONM.

The term "channel" is a programmatic construct and refers to a virtual representation of any anatomical site on a patient's body, which may be an active stimulation site or a reference/pick up site. A channel is a means of identifying and recording a signal with respect to active and reference body sites. Each channel may be defined by a channel ID, comprising a unique identifier for the channel; a channel name; an active body site ID, comprising a unique identifier for the channel's active body site; and, a reference body site ID, comprising a unique identifier for the channel's reference body site.

The term "trace" refers to an array of recorded data associated with a channel. A trace represents the data recorded over the channel over a specific amount of time. Each trace may be defined by a time stamp, indicating the moment in time when the trace was collected; a channel defining the channel associated with the trace; a sweep, indicating the duration of time(s) used to record the trace's data; and, trace data, comprising an array of recorded data points for the trace.

The term "sweep" refers to a plurality of traces recorded over a particular period of time.

The term "trial" refers to a grouping of data recorded by multiple channels over a same span of time. A standard trial represents the traces from one or more channels of a specific mode (one or more trials) captured over the same span of time. Each trial may include: a time stamp, indicating the moment in time when the trial was collected; and, traces, comprising an array of traces captured for the trial.

The term "mode" refers to one or more trials. A mode represents a specific way for storing and displaying data from a simulation system. Each mode may include: a mode ID, comprising a unique identifier for the mode; a mode name; a mode type, such as lower somatosensory evoked potential (SSEP), electromyograph (EMG), or electroencephalograph (EEG); and mode trials, comprising an array of standard trials acquired for the mode, if any, Data generated by simulation systems of the present specification are routed to a collection of modes, wherein the modes contain a collection of time stamped trials including a collection of traces wherein each trace contains data associated with a specific channel. To display generated data to a user, the system queries the collection of trials for time stamps that fall within a requested time span or time window and then displays the data on a graphical user interface (GUI). Generated data is stored within a trace array associated with a given channel.

In embodiments of the present specification, the simulation systems comprise programmatic instructions stored in a tangible, non-transitory computer readable medium, wherein the programmatic instructions define a plurality of channels, each of said channels being virtually representative of an anatomical site of the patient, and wherein, when executed, the programmatic instructions are configured to simulate a patient's response to one or more stimuli over a simulation timeframe.

The present specification provides a software-based medical training simulator for neurodiagnostic testing and intraoperative neurophysiological monitoring. This software simulator differentiates itself from currently available training tools because it does not require connection to any neurodiagnostic or IONM hardware, thereby reducing the barrier to access for training centers and individuals. The software simulator comprises simulations of a wide range of technical, anesthetic, and surgical events likely to be encountered during typical use of the simulator.

While the present specification is directed toward simulation of IONM systems, the systems and methods disclosed herein may also be applied to other neuromonitoring techniques and systems and are not limited to only IONM simulation. For example, in some embodiments, the systems and methods of the present specification may be applied to simulation of electromyography (EMG) monitoring. In some embodiments, IONM may be viewed as an umbrella system which contains the capabilities of an EMG plus additional features. In some embodiments, the systems and methods of the present specification may be applied to simulation of spinal surgery and, in particular, events specifically related to potential problems encountered in spinal surgeries.

In various embodiments, the present specification provides a training module that simulates the effect of likely events and rare events encountered in a clinical environment on waveforms recorded in an IONM system. The training simulation enables trainees to learn how medical instruments operate, as well as how patients respond to environmental changes and how a medical instrument and the corresponding waveform recording in an IONM system are affected by technique and choice of parameters. The training simulator enables trainees to learn what is a normal effect and what changes are significant, how to troubleshoot, and when to inform a surgeon or an anesthesiologist, with the understanding that different patients and different disease states will affect every aspect of the monitoring from setup to operation to interpretation.

In various embodiments, the software simulator operates by reducing the number of computations required to provide training, so that the training simulator may simulate a real-time patient monitoring environment.

The training simulator of the present specification provides a safe, controlled, patient-free and neurodiagnostic/IONM equipment-free training experience with a wide spectrum of types of events and intensities of each event, which enables trainees to learn to recognize cause and effect relationships between events, and the required responses to the same. The simulator provides a learning experience to the trainees by using the same workflow and tools that the trainees use in the real clinical environments. This results in more efficient, accessible, cheaper, and higher quality training programs.

In various embodiments, the simulator provides a self-guided mode, as well as an instructor-led mode, for trainees. In both modes, effects can be customized so the trainee can experience realistic events they are likely to encounter in a real clinical environment.

The training simulator of the present specification has a unique physiologic model, wherein details corresponding to parameters such as, but not limited to, effects of injury, environmental changes, and underlying nervous system characteristics may be varied. In an embodiment, as a simulator for IONM, effects comprise adjusting one or more variables that may impact neurological output readings, including, but not limited to, anesthesia agents, patient temperature, patient positioning, technical setup (plug-in) errors for inputs and outputs, electrosurgery interference, mains interference, EMG muscle activity, or pedicle screw stimulation with or without breach. For example, it should be appreciated that poor patient positioning can cause cardiovascular and pulmonary changes to the associated extremity or part of the body, affecting recorded signals during IONM. Similarly, with respect to temperature, a reduction in core body temperature can affect recorded signals in IONM. Additional effects comprise pre-existing conditions and surgical injuries. In embodiments, customizable parameters of the training simulator comprise the timing of onset, duration, intensity, and offset of each of these effects. In various embodiments, scripts used to create a series of steps for demonstration or assessment may be saved and reused to compare effectiveness of training for a specific trainee.

In various embodiments, the training simulator of the present specification responds simultaneously and accurately to any mix of inputs and outputs, allow complex simulation easily (by virtue of signal pruning and scheduling steps), allows modular granularity to add features to enhance realism, supports non-linear and discontinuous effects and short and long term phenomenon. In various embodiments, the training simulator of the present specification supports patient and drug specific effects, such as neuropathy and the varying effects of drugs on different people, supports specific anatomic defects, such as missing limbs, neural anastomosis, skull defects, and spinal cord injury, and accounts for location and type of insults and propagates location specific insults properly. In various embodiments, the training simulator of the present specification uses body sites and signal generator sites as elements of computational processes, as described further herein. In various embodiments, the training simulator of the present specification computes signal alteration with distance and orientation, uses stimulator intensity and other characteristics and established signal response curves to generate signals which are appropriate to stimulus, allows arbitrary stimulus input location and types and arbitrary response pick up sites and accurately synthesize responses, simulates stochastic and random events which generate signals (including a variety of artifacts) that are seen in actual circumstances, allows physiologic time constants for changes to be represented over real time, accelerated time, or to be immediately applied or removed, supports multiple anesthetic effects, such as slowing nerve conduction velocity, reduced responsiveness of critical neurons, muscle blockade effects from neuromuscular junction drugs, and cortical burst suppression, on each of several different models to accurately synthesize their effects. In various embodiments, the training simulator of the present specification supports manual, scripted and flow controlled effects, tracks time of effect and time of user response to effect for evaluation, records entire session for scoring and reviews, and supports alternative scenarios for any given state. In various embodiments, the training simulator of the present specification supports all major insults and physiologic changes seen in actual patients including, but not limited to: temperature, blood pressure, heart rate, heart rhythm, blood supply, pressure applied to body parts, nerve stretch, nerve severing, screw placement (and misplacement), and nerve location. In various embodiments, the training simulator of the present specification uses graphical interface to represent operator (surgeon) activities that will affect the system, allows use of actual patient responses that are then modulated by other inputs so that non-classical responses can be seen, and supports "video" input and "video" synthesis for surgical procedures and for physical responses (for example, thumb twitch, jaw clench) that are part of a user's normal input. In various embodiments, the training simulator of the present specification supports interactive scripting. For example, the system can ask a user to identify a problem, ask if they want to communicate with a surgeon or anesthesiologist, and perform interaction necessary during monitoring that is not part of operating the IONM instrument. In various embodiments, the training simulator of the present specification provides for simulation that can be stopped, studied, preserved and restored.

Figure 1B:
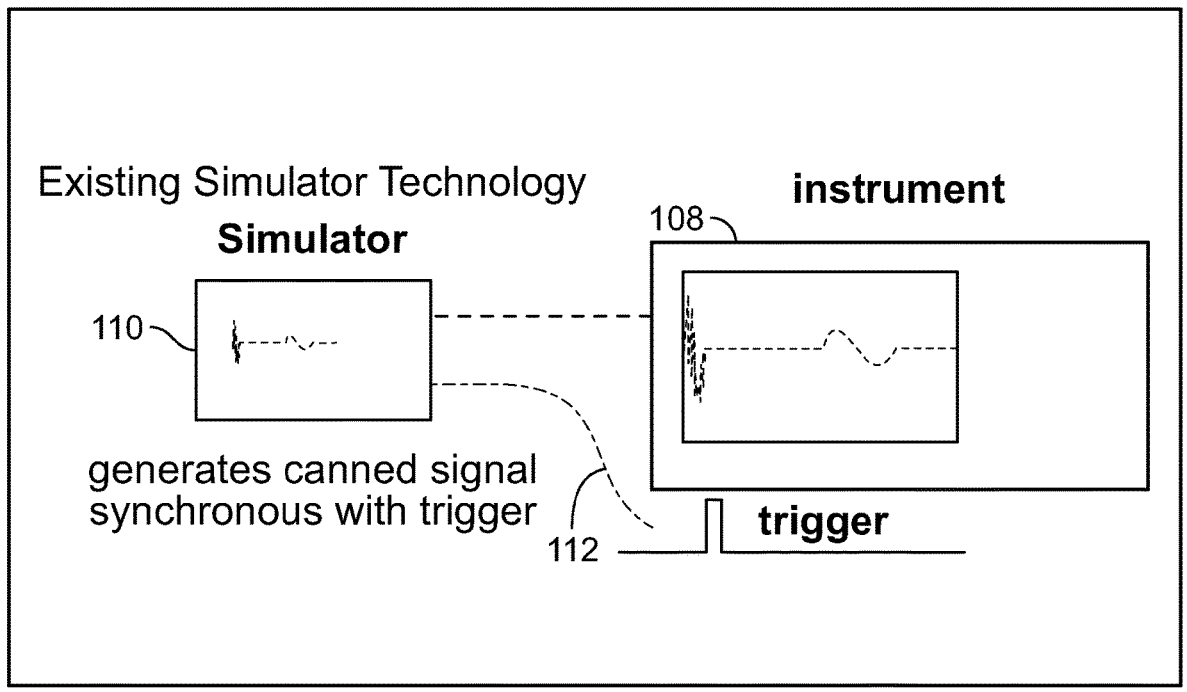
FIG. 1B illustrates a conventional simulator of an IONM system.
Figure 2:
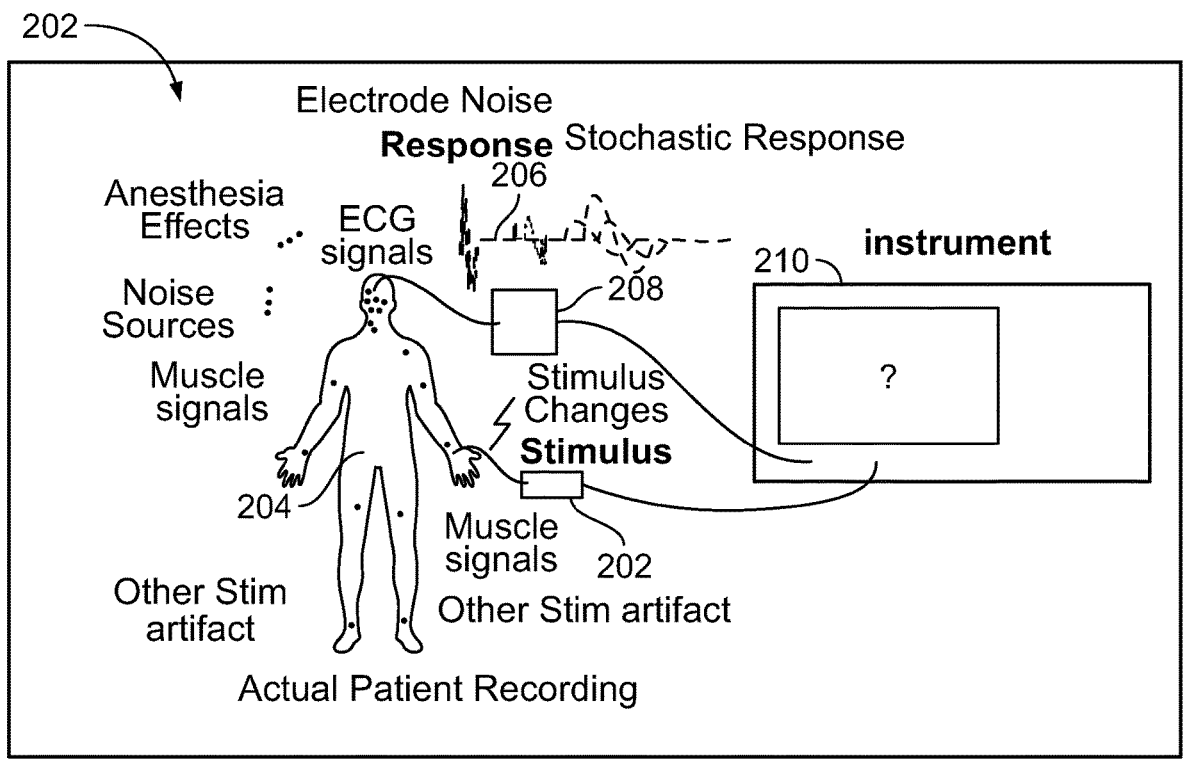
FIG. 2 illustrates a real person being monitored via an IONM system.

Referring to FIGS. 1A, 1B, and 2, in conventional IONM system simulators, a pre-defined response is mixed with random noise and is fed back to the IONM instrument. The underlying response is found by averaging and filtering for teaching the trainees how to use the instrument. However, the response on the instrument does not simulate an actual patient, as the responses are 'canned' or pre-recorded and only a small number of responses are made available to illustrate features of the recording instrument. However, when a real patient is being monitored via an IONM system, a multitude of input signals are received by stimulus pick up body sites, such as the patient's brain, and corresponding response waveforms are generated. Conventional wisdom is that it is not possible to simulate the receiving and processing of the multitude of input stimuli to produce a synthesized waveform for display because such processing is an n-factorial problem. The number of cases needed to represent combinations of input stimuli parameters is unmanageable for conventional training simulation system as significant computational power is needed to simulate highly connected systems.

The training simulator of the present specification takes into account multiple components that generate signals de novo or in response to various stimuli. In order to produce a response waveform on the instrument of an IONM system, the training simulator enables the multiple components (such as but not limited to, brain, sensory and motor cortex, spinal cord, anterior horn cells, branching plexi for both upper and lower extremities, nerves, myo-neural junction and muscle) to communicate with each other, modeled in ways that accurately represent each component's response and responsiveness. For example, nerves conduct, then trigger the myo-neural junction, which activates a muscle.

In various embodiments, the attributes of each individual component are tabulated, and the effect of all modifiers, (such as but not limited to, temperature, anesthesia, and stretch) are specified individually in the training simulator of the present specification.

In an embodiment, the response at any stimulus pick up site on a human body is the weighted sum of all signals that are detectable at that site. In an embodiment, the detectable signal is attenuated and filtered based on distance and geometry. Geometry includes electrode orientation and muscle or nerve orientation, and the effects of obesity, neural anastomosis and other atypical neural anatomies. The simulated pick up computes the weighted contributions of every item that may add to the response. The responses are time stamped which allows decoupling time of acquisition from time of arrival. In other words, expected results are calculated before they would occur and are then time stamped, saving computational time. As a result, the simulator generates responses asynchronously, and the multiple levels and stimulus sites are computed sequentially instead of concurrently. The simulated instrument of the training simulator of the present specification reads time stamped responses and realigns them in time. This process is asynchronous rather than real-time which reduces peak computational levels.

In embodiments, the training simulator operates by generating a simulated, or virtual, response at one or more reference sites by one or more signal channels to at least one simulated, or virtual, stimulation at a stimulation, or active stimulation, site by an active signal channel within a time window of a simulation time frame. The simulation systems and methods of the present specification reduce the computational power required, and therefore reduce the cost and time needed, to provide a robust and meaningful simulation by: first eliminating, or 'pruning', reference signal channels producing too low of a response to be consequential, thereby decreasing the total number of channels required to be monitored; and, then calculating an expected response to at least one simulated stimulus for presentation to the system at a requested time, wherein the calculation is performed by running algorithms which generate, before some future time, an expected response at the one or more reference sites to the simulated, or virtual, stimulation at the stimulation site at the future time.

The first step of eliminating, or pruning, reference signal channels having too low of responses is based on geometric/distance relationships between the reference sites and the stimulation site. The calculation at the second step is buffered and time stamped with the future time so that it may be presented when the associated time window is requested by the system. The system is constantly calculating expected reference signal channel responses to virtual stimuli in advance of the expected response time. By calculating virtual responses ahead of time, the system eliminates the need of having to calculate responses in real time. Calculating the virtual responses in advance of when they would actually occur widens the allowable amount of time to complete computations which require high accuracy and allows the system to present the complete, calculated response once the response time window is requested. In embodiments of the present specification, the second step of calculating responses in advance of their actual response time is referred to as 'scheduling', producing 'scheduled' responses and differs from 'triggering' producing 'triggered' responses, wherein responses are calculated at the time they would occur. In embodiments, scheduled signals are processed sequentially rather than concurrently, with respect to the time of response, which is done with triggered responses.

In some embodiments, the pruning step may decrease the total number of reference channels required to be monitored from several hundred to a few dozen, thereby greatly reducing the computational load placed on the simulation system. In an example, a simulation system comprises one active channel, designated as Channel 1 and associated with a patient's thumb, and fifty reference channels, designated as Channels 2-51, as defined by a user. At the first step, or pruning step, the system models how an electrical stimulation of one or more stimuli to the thumb, designated as Channel 1, would affect reference Channels 2-51, using predefined algorithmic interrelationships between Channel 1 and each of Channels 2-51. In embodiments, the algorithmic interrelationships are based on geometry, for example, which side of a patient's body is being stimulated and which side of the body the response is being measured (ipsilateral or contralateral) and on the distance between the stimulation site and each of the reference sites. Once the system determines the physiological responses at each of the reference channels, it decides what subset of Channels 2-51 to actually use moving forward based on at least one threshold response level. Channels producing responses below the threshold level are eliminated, or pruned, while the channels producing responses at or above the threshold level are kept for the next step. This pruning step insures that the system need not go through the heavy work of calculating responses at all channels when many of them may not have any responses worth recording. In the present example, the system has kept reference Channels 2-10 as they produced responses at or above the threshold and eliminated reference Channels 11-51 from consideration as they produced responses below the threshold level, causing the system to determine these channels do not produce a consequential or meaningful response.

Once the pruning step is completed, the system runs the simulation and does so by identifying what signals may affect each channel and when those affects would occur, designated in embodiments as time T1, and then calculating the physiological response of each channel to those signals before time T1. In various embodiments, identified signals are characterized by parameters that include, but are not limited to, amplitude, distance from the affected channel, when the response signal will occur in the future (T1), and waveform shape.

In various embodiments, the signals that can affect each channel are functions of one or more of the following: body positioning, signals from other channels, shock artifact, a muscle response (typically in a range of 5 to 15 mV, and preferably 10 mV), a nerve response (typically in a range of 5 to 30 microvolts, preferably 20 microvolts), brain responses, anatomic defects, such as missing limbs, neural anastomosis, skull defects, or spinal cord injuries, including variables that account for a location and/or type of insult, nerve stretch, nerve severing, screw placement (and misplacement), nerve location, or an amount of pressure applied to body parts.

In various embodiments, physiological responses of all selected channels may also be affected by global modulators such as one or more of the following: a patient's age, gender, body temperature, blood pressure, heart rate, heart rhythm, or blood supply, whether the patient has been administered anesthesia, including the specific volume and anesthesia type and multiple anesthetic effects, such as slowing nerve conduction velocity, reduced responsiveness of critical neurons, muscle blockade effects from neuromuscular junction drugs, and/or cortical burst suppression, whether the patient is under the influence of illicit or recreational drugs and, if so, the specific type and volume of drugs, or one or more patient disease states, including neuropathies, diabetes, HIV, or cancer.

Therefore, in embodiments, at each channel, the system records multiple physiological responses (each a result of possibly a different signal) that are added together to generate a time stamped data stream. This allows the system to calculate physiological responses ahead of time, buffer that data, and then produce it when the system requests that specific time window. For example, at a Time Window 1, the system has propagated a physiological response from Channel 3 to multiple other channels. At a Time Window 2, the system identifies the physiological response from Channel 3 as a signal that may affect Channel 2 in 10 milliseconds because it is a 10 mV stimulation that will take 10 milliseconds to propagate to Channel 2. Rather than waiting the 10 milliseconds to elapse in order to determine the effect on Channel 2, as is done in conventional simulation systems, the simulation system of the present specification immediately calculates what the physiological effect will be but time stamps it so that the system knows it will actually occur in 10 milliseconds. The system is constantly calculating how various signals may affect a channel in advance of the actual response time and not in real time when the response would occur.

Simulator System Architecture

Figure 3A:
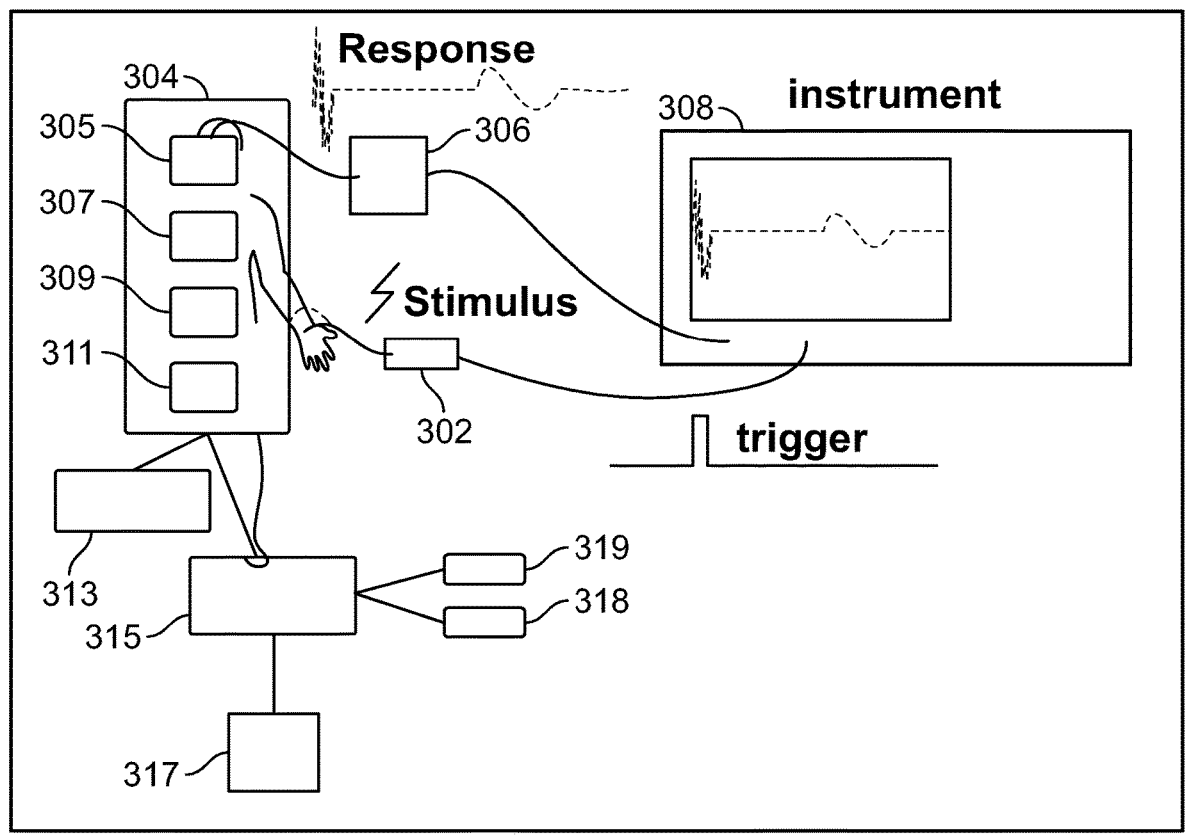
FIG. 3A is a block diagram illustrating an IONM training simulator, in accordance with an embodiment of the present specification.

FIG. 3A illustrates an exemplary system environment for implementing a software-based medical training simulator for neurodiagnostic testing and IONM, in accordance with some embodiments of the present specification. In the methods and systems of the present specification, a stimulus 302 is provided to an IONM training system 304. IONM training system 304 may be a computing system that is fixed or portable. In various embodiments, system 304 comprises at least one processor 305, at least one non-transitory memory 307, one or more input devices 309 (such as, but not limited to, a keyboard, mouse, touch-screen, camera and combinations thereof) and one or more output devices 311 (such as, but not limited to, display screens, printers, speakers and combinations thereof), all of which may be stand-alone, integrated into a single unit, partially or completely network-based or cloud-based, and not necessarily located in a single physical location. In an embodiment, system 304 may also be in data communication with one or more databases 313 that may be co-located with system 304 or located remotely, such as, for example, on a server. In various embodiments, a plurality of systems 304 and client computers may be used to implement the training simulator of the present specification.

Figure 3B:
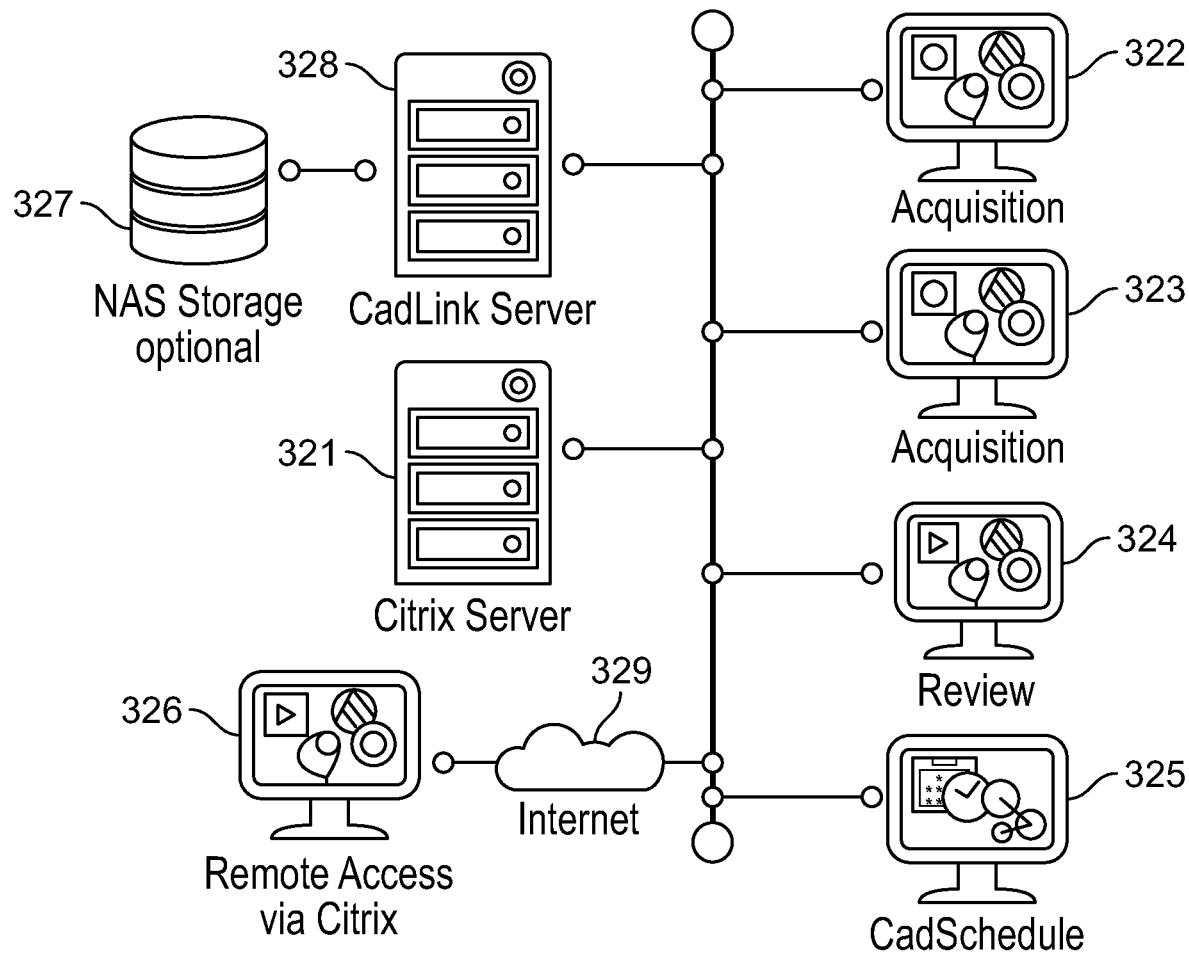
FIG. 3B illustrates a first exemplary network configuration for use with an IONM training simulator, in accordance with embodiments of the present specification.

For example, FIG. 3B illustrates a first exemplary network configuration 320 for use with an IONM training simulator, in accordance with embodiments of the present specification. The first exemplary network configuration 320 depicted in FIG. 3B may be used in a large clinic or lab, comprises five clients 322, 323, 324, 325, 326, and provides for remote access via a first server 321. In some embodiments, the first server 321 is a Citrix® server. The first server 321 is in data communication with, and provides for data communication, via an Internet connection 329, between, the clients 322, 323, 324, 325, 326 and a second server 328, which is in further data communication with a network-attached storage (NAS) 327. In embodiments, first and second clients 322, 323 comprise acquisition devices and include IONM training simulators, similar to IONM training system 304 of FIG. 3A, a third client 324 comprises a review device, a fourth client 325 comprises a scheduling device, and a fifth client 326 comprises a remote access device which accesses the other devices of the first exemplary network configuration 320 via Citrix®.

Figure 3C:
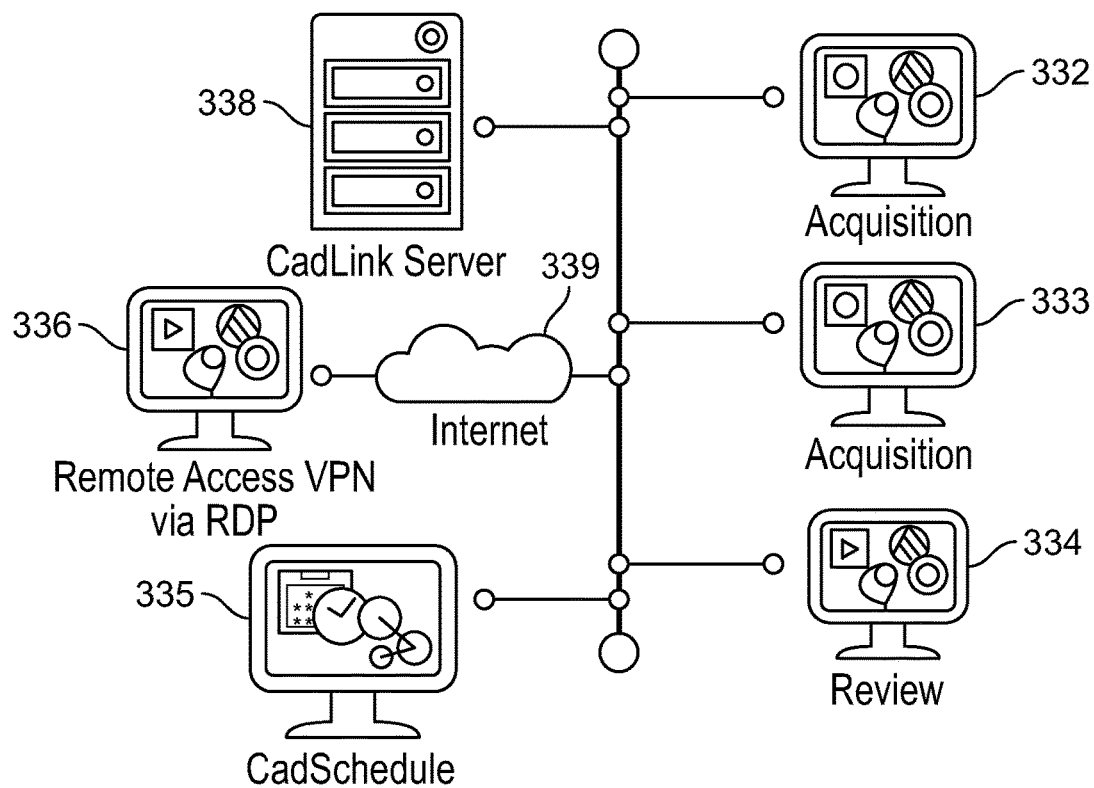
FIG. 3C illustrates a second exemplary network configuration for use with an IONM training simulator, in accordance with embodiments of the present specification.

FIG. 3C illustrates a second exemplary network configuration 330 for use with an IONM training simulator, in accordance with embodiments of the present specification. The second exemplary network configuration 330 depicted in FIG. 3C comprises a dedicated server 338 and five clients 332, 333, 334, 335, 336 and provides for remote access via a virtual private network (VPN) and remote desktop protocol (RDP). The dedicated server 331 is in data communication with, via an Internet connection 339, the clients 332, 333, 334, 335, 336. In embodiments, first and second clients 332, 333 comprise acquisition devices and include IONM training simulators, similar to IONM training system 304 of FIG. 3A, a third client 334 comprises a review device, a fourth client 335 comprises a scheduling device, and a fifth client 336 comprises a remote access device which accesses the dedicated server 338 via a VPN and RDP connection.

Figure 3D:
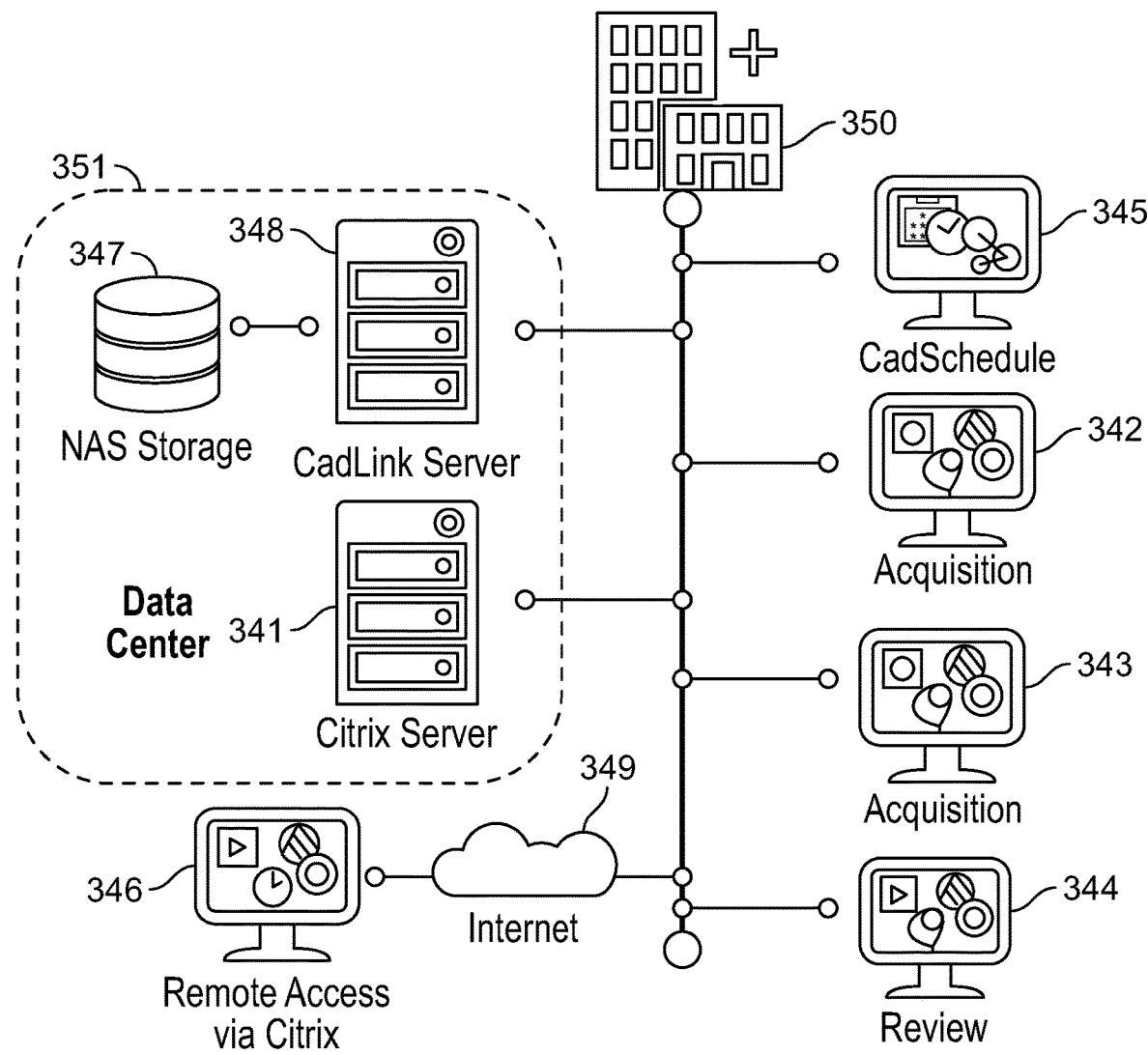
FIG. 3D illustrates a third exemplary network configuration for use with an IONM training simulator, in accordance with embodiments of the present specification.

FIG. 3D illustrates a third exemplary network configuration 340 for use with an IONM training simulator, in accordance with embodiments of the present specification. The third exemplary network configuration 340 depicted in FIG. 3C may be used in a single hospital 350 and comprises an enterprise network comprising five clients 342, 343, 344, 345, 346, and provides for remote access via a first server 341. In some embodiments, the first server 341 is a Citrix® server. The first server 341 is in data communication with, and provides for data communication, via an Internet connection 349, between, the clients 342, 343, 344, 345, 346 and a second server 348, which is in further data communication with an NAS 347. The first server 341, second server 348, and NAS 347 together comprise a data center 351. In embodiments, first and second clients 342, 343 comprise acquisition devices and include IONM training simulators, similar to IONM training system 304 of FIG. 3A, a third client 344 comprises a review device, a fourth client 345 comprises a scheduling device, and a fifth client 346 comprises a remote access device which accesses the other devices of the third exemplary network configuration 340 via Citrix®.

Figure 3E:
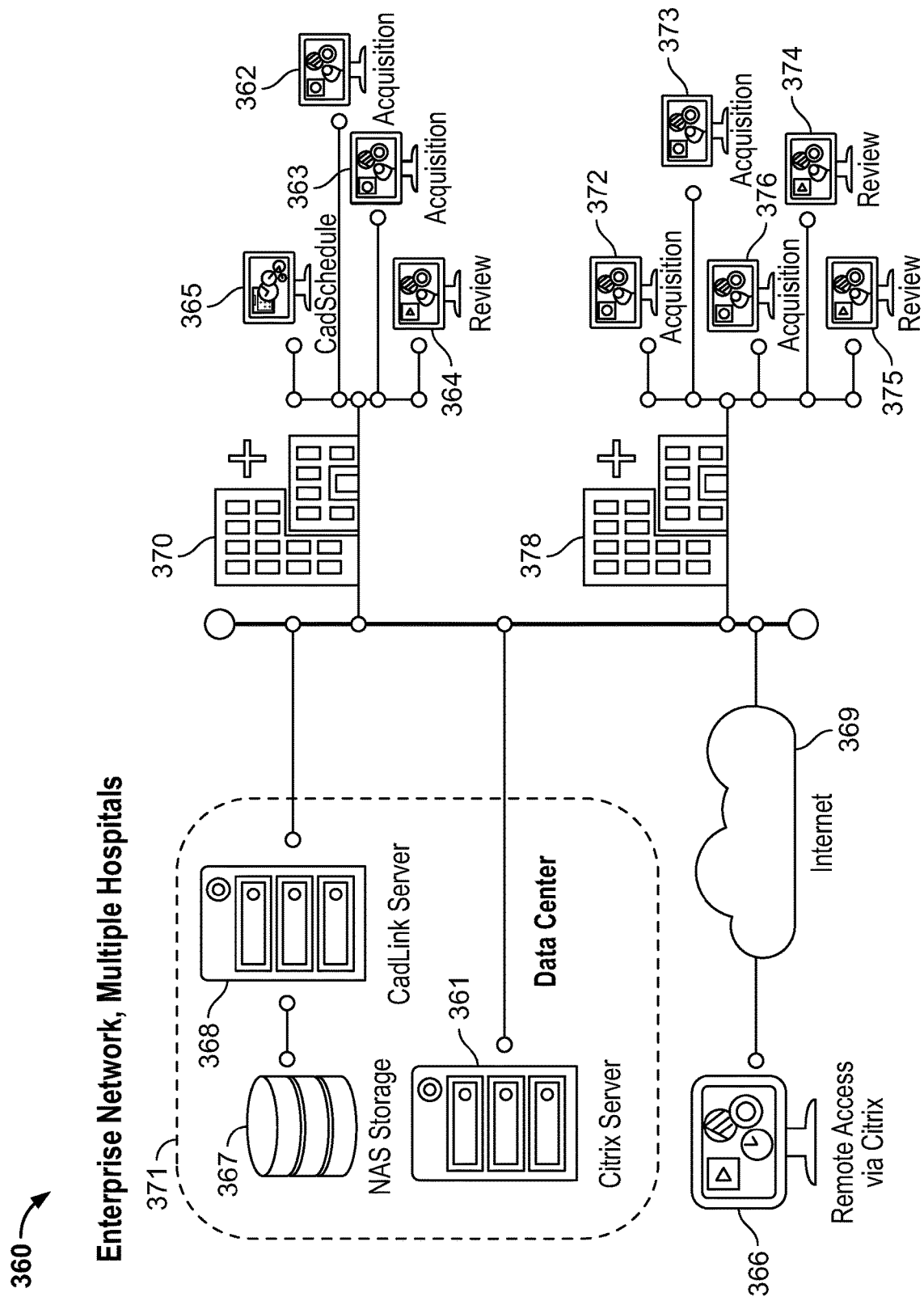
FIG. 3E illustrates a fourth exemplary network configuration for use with an IONM training simulator, in accordance with embodiments of the present specification.

FIG. 3E illustrates a fourth exemplary network configuration 360 for use with an IONM training simulator, in accordance with embodiments of the present specification. The fourth exemplary network configuration 360 depicted in FIG. 3D may be used in a multiple hospitals 370, 378 and comprises an enterprise network comprising: a data center 371 comprising a first server 361, a second server 368, and NAS 367; a first hospital comprising four clients 362, 363, 364, 365; a second hospital 378 comprising five clients 372, 373, 376, 374, 375; and a remote access client 366. In some embodiments, the first server 361 is a Citrix® server. The first server 361 is in data communication with, and provides for data communication, via an Internet connection 369, between, the first hospital 370 and its clients 362, 363, 364, 365, the second hospital 378 and its clients 372, 373, 376, 374, 375, the remote access device 366, and the second server 368, which is in further data communication with the NAS 368. In embodiments, first and second clients 362, 363 of first hospital 370 and first, second, and third clients 372, 373, 376 of second hospital 378 comprise acquisition devices and include IONM training simulators, similar to IONM training system 304 of FIG. 3A. In embodiments, third client 364 of first hospital 370 and fourth client 374 of second hospital 378 comprise review devices. In embodiments, fourth client 365 of first hospital 370 and fifth client 375 of second hospital 378 comprise scheduling devices. In embodiments, remote access device 366 accesses the other devices of the fourth exemplary network configuration 360 via Citrix®.

Referring now to FIGS. 3B-3E simultaneously, the second servers allow users to monitor or review simulation data (acquired via the acquisition devices), either locally via the review devices or remotely via the remote access devices. The remote access devices allow users to remotely monitor a patient's neurophysiological status during a simulation (or during an actual surgery). In some embodiments, review devices and remote access devices allow users to change data views and create reports, but control of the simulation is only possible at the acquisition devices. The scheduling devices allow users to schedule appointments and manage resources across hardware, personnel, and locations. Simulation data is stored on the NAS. In some embodiments, simulation data is first stored locally in local databases on the acquisition devices and also streamed to the NAS. In some embodiments, once a simulation case is closed and has been fully uploaded to the databases, it is removed from the local databases. In some embodiments, the network configurations provide for auto-archiving of simulation or patient data. In some embodiments, the client devices provide health level seven international (HL7) interfaces to connect with electronic medical records (EMR), to allow for patient demographics to be received and reports to be returned. While configurations with four or five client devices are illustrated, the systems and methods of the present specification are configured to support, and may include, any number of client devices. In some embodiments, the network configurations provide support for a range of 1 to 30 client devices.

Figure 3F:
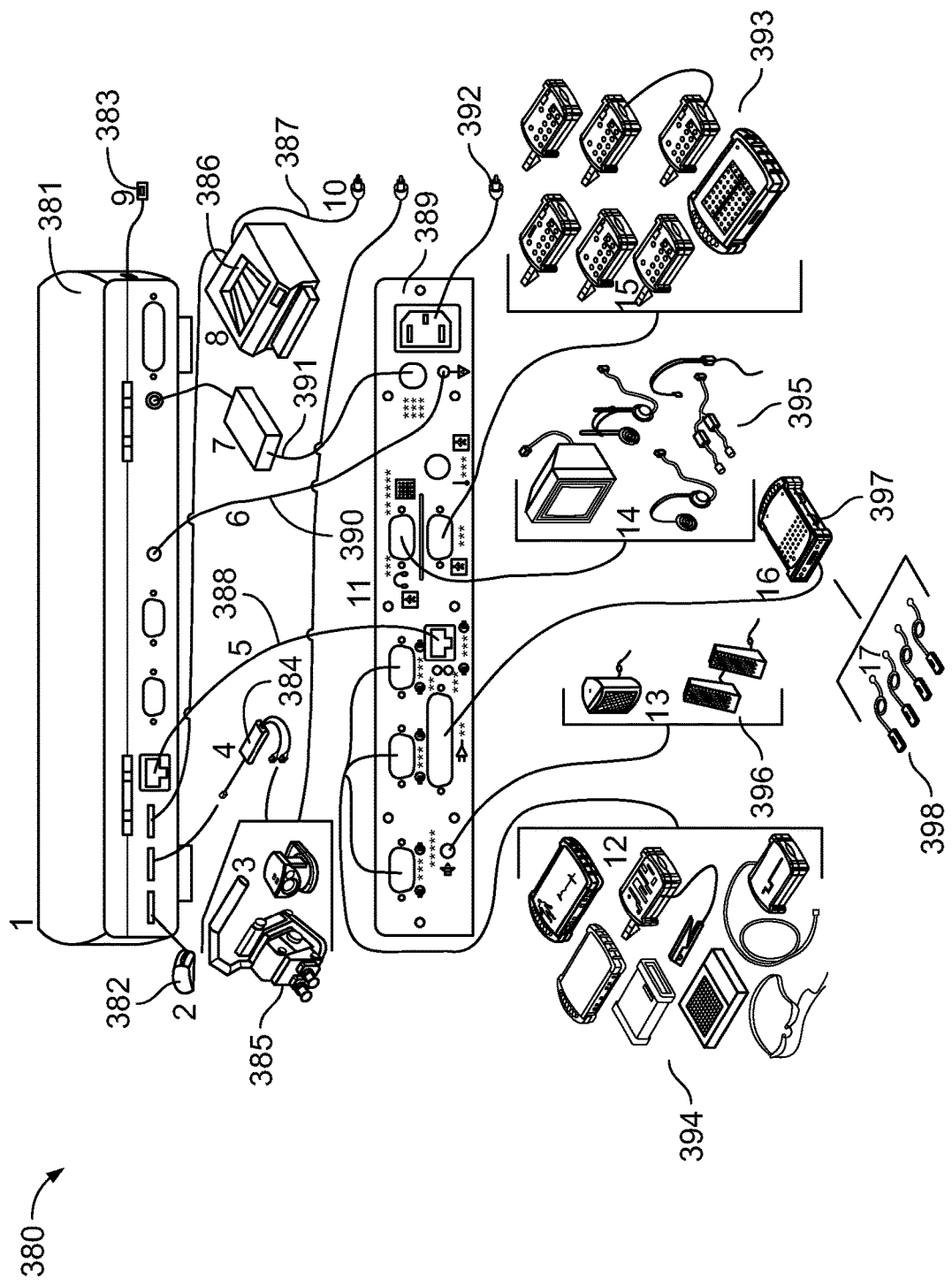
FIG. 3F illustrates an exemplary configuration of an IONM training simulator system connected to a client device.

FIG. 3F illustrates an exemplary configuration 380 of an IONM training simulator system connected to a client device 381. In embodiments, the client device 380 comprises a laptop or desktop computer. An input device 382, such as a mouse, is connected to the client device 381. In embodiments wherein the client device comprises a desktop computer, the input device may further comprise a keyboard and a display may also be connected to the client device. The client device 380 further includes a first Internet connection 383 to a network. In embodiments, a USB adapter 384 provides for connectivity to a first set of visual stimulators 385 for providing evoked potential visual stimulation to a patient (or for providing simulation). In embodiments, a printer 386 with printer power cable 387 is connected to the client device 381 for printing simulation results. The client device 381 is connected via second Internet connection 388 to an IONM simulation module 389 to enable network communication with the simulation module 389 and a network. Client device 381 is also connected to the simulation module 389 via ground wire 390 and a first power cable 391 to provide ground and power to the simulation module 389. The first power cable 391 is only required when the client device is a laptop. When the client device is a desktop computer, power is supplied to the simulation module 389 via second power cable 392, which is plugged in directly to a power outlet. A first electrical stimulator 393 is connected to the simulation module to provide electrical stimulation (or simulate electrical stimulation). In some embodiments, additional electrical stimulators 394, for example high voltage stimulators, are connected to the simulation module 389 via auxiliary inputs to provide (or simulate) additional electrical stimulation. A second set of visual stimulators or auditory stimulators 395 are connected to the simulation module 389 to provide evoked potential visual or auditory stimulation (or simulation). In some embodiments, a set of speakers 396 is connected to the simulation module 389. A detector module 397, including attached detector clips 398, is connected to the simulation module for recording patient responses (or simulating patient responses).

Referring back to FIG. 3A, in embodiments, system 304 enables multiple components, such as but not limited to, brain, sensory and motor cortex, spinal cord, anterior horn cells, branching plexi for both upper and lower extremities, nerves, myo-neural junction and muscle, to communicate with each other, modeled in ways that accurately represent each component's response and responsiveness. For example, nerves conduct, then trigger the myo-neural junction, which activates a muscle. Unlike conventional systems, such as those illustrated in FIGS. 1A and 1B, system 304 provides a graphical user interface, which may be integrated into an input device 309, such as a touch-screen, to a user to configure a patient scenario by simulating a patient's physiological condition, neurological condition, or other conditions. The attributes of each individual component may be tabulated, and the effect of all modifiers, such as but not limited to, temperature, anesthesia, and stretch, may be specified individually through the user interface of system 304. A multitude of patient parameters may be configured through the user interface provided by system 304. Stimulus signals 302, received by system 304, may emulate, and are not limited to, electrode noise, anesthesia effects, EEG signals, muscle signals, other noise sources, and other stimulating signals which can be received by a real patient. The signals generated by system 304 include the signals that would cause a real patient's brain to produce a plurality of stochastic responses which can be captured by an electrode 306.

A neurological response simulated by system 304, in response to stimulus 302, is collected via electrode 306 and is displayed as response waveforms on a display device 308. In some embodiments, display device 308 is a part of an IONM system. The responses simulate an actual patient's responses to physiological, neurological, and other external parameters, which are configurable by users of system 304. Since the patient parameters are configurable across a multitude of variables, the corresponding responses are not limited to pre-recorded responses.

Referring again to FIG. 3A, system 304, which may also be referred to herein as stimulator 304, is in some embodiments, connected to a server 315. In some alternative embodiments, system 304 operates on its own, and the functions implemented by the server, as described herein, are implemented by system 304.

In an embodiment, the server 315 stores and executes programmatic instructions for: simulating a plurality of input stimulus generation sites on a body; simulating a plurality of input stimulation pick up sites on the body; wherein the input stimulus generation sites and the input stimulation pick up sites have specified relations to each other and to other non-neurologic structures of the body (e.g. skin, bone, fat). In some embodiments, the server also comprises programmatic instructions which, upon execution, generate response waveforms corresponding to the input stimulations picked up at the input stimulation pick up sites. The response waveforms are displayed on display 308 of the IONM instrument coupled with the server. In some embodiments, the response waveforms are displayed on a display of system 304, or on any other display connected to the server.

In an embodiment, one or more client computers 317 may be coupled with the server and an instructor may use system 304 with one or more trainees by manipulating a control panel running on system 304, to simulate a series of events, with or without visibility of these changes to the trainees, wherein each trainee can view the corresponding response on a client computer 317.

In an embodiment, the server 315 is configured to be coupled with either stimulator splitters 319 or ES-IX stimulators 318. In an embodiment, the server 315 is configured to be coupled with four auditory stimulators, such as but not limited to, insert earphones for intraoperative neuromonitoring of auditory evoked potentials. In an embodiment, the server is configured to be coupled with four visual stimulators, such as but not limited to, visual evoked potential (VEP) goggles for monitoring of visual evoked potentials. In embodiments, the server is configured to be coupled with transcranial stimulators, electrical stimulators, or evoked potential stimulators (audio and video). In various embodiments, multiple configurations of the server may be set up by a user/trainee.

Simulator Method

Figure 4A:
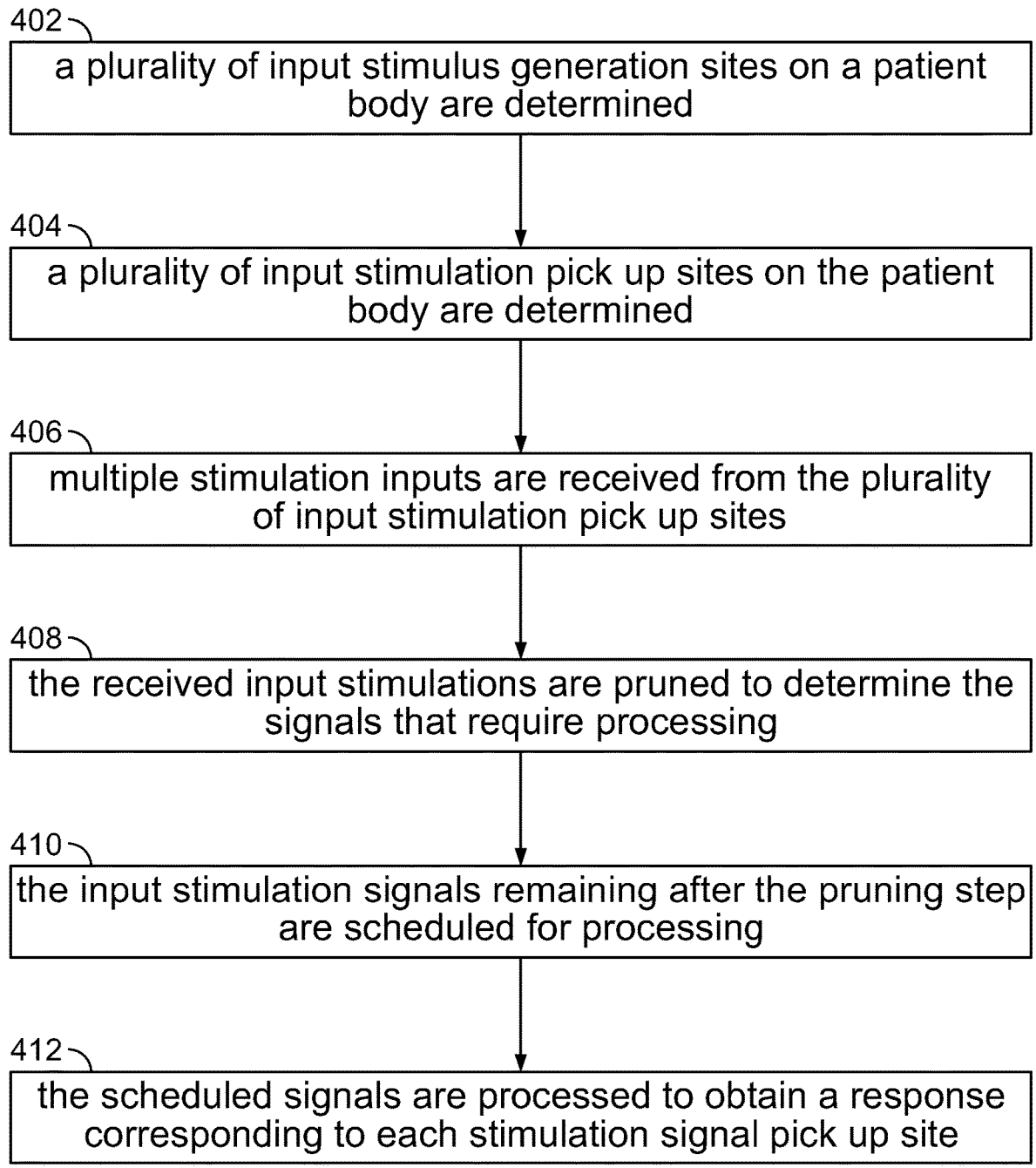
FIG. 4A is a flowchart illustrating the operational steps of an IONM training simulator, in accordance with an embodiment of the present specification.

FIG. 4A is a flowchart illustrating the operational steps of an IONM training simulator, in accordance with an embodiment of the present specification. At step 402, a plurality of input stimulus generation sites on a patient body are determined. In various embodiments, exemplary input stimulus generation sites include, but are not limited to, a posterior tibial nerve, a median nerve such as the median nerve, an ulnar nerve, an auditory nerve, an optic nerve, and a motor cortex, at sites including arms, legs, head, and wrists. At step 404, a plurality of response pick up sites on the patient body are determined. In various embodiments, some exemplary response pick up sites may include, but are not limited to, Erb's point, a patient's scalp, a sensory cortex, an auditory cortex, a visual cortex, a brainstem, a cervical spinal cord, and peripheral nerves. The input stimulus generation sites and response pick up sites have predefined relations to each other and to other non-neurologic structures of the body, such as skin, bone, fat, and others. In embodiments, the predefined relations stem from known nervous system anatomical pathways between structures. In an exemplary predefined relation, median nerve stimulation is expected to generate an Erb's point response ipsilaterally and a somatosensory cortical response contralaterally. At step 406, multiple inputs are received from the plurality of stimulation and response pick up sites.

At step 408, the received stimulations are pruned to determine the signals that require processing. The step of pruning enables determining the stimulation signals that require processing, while the remaining ones can be ignored. In embodiments, pruning comprises attenuating and filtering the input stimulation signals based on signal strength, wherein the system evaluates each signal in relation to at least one signal threshold, wherein signals at or above the threshold are retained for processing while signals below the threshold are removed or ignored. Signal strength, in turn, is based on the relationships or interrelationships of the stimulation site and the response or pick up sites which, in embodiments, comprise distance and geometry, wherein geometry includes electrode orientation and muscle or nerve orientation, and the effects of obesity, neural anastomosis, and other atypical neural anatomies on signal strength and distance is defined as the distance of an active stimulation site from a signal reference or pick up site.

In an embodiment, the received input stimulation signals are pruned based on a distance of a generation of a signal from the signal pick up site, as the size of a signal decreases as the distance of signal active stimulation (generation) site increases with respect to the signal pick up site. In an embodiment, a predetermined geometric relationship between the signal generation site and the signal pick up site and, a predefined distance between the two sites, is used to determine the input stimulation signals that require processing to produce a response waveform. For example, in an embodiment, stimulation of a left median nerve would produce results from an ipsilateral brachial plexus, ipsilateral cervical nerve roots, spinal cord, and a contralateral somatosensory cortex. Waveforms would not be expected from the right arm or legs. Stimulating the left median nerve at the elbow would result in responses at a brachial plexus (Erb's point), cervical spine, and contralateral somatosensory cortex), but not at the left wrist because this is an ascending (afferent) sensory pathway. Similarly, monophasic transcranial stimulation of the motor cortex will result in responses from muscles on the contralateral side of the body only, whereas biphasic transcranial stimulation will result in bilateral muscle responses.

In embodiments, the predefined distance is calculated based on a model of the average adult human body, where the model uses the distance between two sites based on their anatomical location. In an example, a contralateral Erb's point sensor will have an attenuated response due to its relatively large distance from any source generator and would be removed from the calculation. The ipsilateral Erb's point would be 2 cm from a nerve generating the response, while the contralateral Erb's point would be 20 cm from the same nerve. In some embodiments, the relation, as a percentage, of a contralateral signal relative to an ipsilateral signal may be calculated as the square of the distance of the ipsilateral point from the nerve generating the response divided by the distance of the contralateral point from the nerve generating the response. Therefore, in an embodiment, the detected signal at the contralateral site would be (2/20) squared, or 1%, of the detected signal at the ipsilateral site. The numerical values would be 10 µV ipsilaterally and 0.1 µV contralaterally.

In an embodiment, an amplitude of the received input stimulation signals is considered for determining whether the signal requires processing. In an embodiment, input stimulation signals having an amplitude larger than a predefined threshold amplitude are processed even if the distance between the generation and pick up sites of these signals is less than the predefined distance threshold. A predefined threshold amplitude may be based on known clinical norms. In embodiments, the threshold is defined as the minimally acceptable amplitude of a nerve somatosensory evoked potential (SSEP) waveform response, as determined by an experienced clinician. Typically, the threshold is in the range of 1-3 microvolts in amplitude using 15 mA of stimulation. In an example, a response for a median nerve SSEP stimulation will be obtained with a stimulus intensity of 15 mA on a normal patient, but a response will be absent using 5 mA stimulus intensity. In some embodiments, the stimulus itself is often several volts, and would be detectable as 'shock artifact' at large distances. In the example above of the distance of Erb's point from a nerve generating site, 1% of a 1 volt stimulus would be 10,000 µV and would be added to the response. The step of pruning reduces the number of received input stimulation signals that require processing, thereby decreasing the computational load.

At step 410, the input stimulation signals remaining after the pruning step are scheduled for processing. Scheduling comprises calculating expected responses, to at least one stimulus at an active stimulation site, at response or pick up sites before the time they would actually occur, time stamping the calculated responses with a time window of when they would occur, and buffering or caching the calculated responses for presentation when the time window is requested by the system. In an embodiment, a time window is built around each input signal by using a pre-defined body model which enables computing said signals at predefined time intervals only. In an embodiment, scheduling comprises applying a time stamp to each input stimulation signal such that these signals can be processed serially to produce a simulated response. Referring again to the above example, the Erb's point signal may take 10 msec to travel from the wrist. Therefore, the synthesizer may be programmed to add the expected response beginning 10 msec into the signal. In some embodiments, scheduling for the synthesizer requires changing an offset rather than actually waiting for time to elapse. Hence, the constraint of real time processing of multiple inputs is avoided. With fewer real time constraints, the parameters that change slowly, including global modulators such as body temperature and anesthesia levels, can be updated infrequently, typically once a second in some embodiments, but are applied to the scheduled responses as if they were updating continuously. Other simulated phenomenon including sounds and video may also be scheduled, allowing very tight time correlation without having overly expensive simulation hardware.

The scheduled stimulation signals and the relationships among the signals represent a manageable computational load which provides a near real-time understanding of the responses generated by a patient, if the patient is stimulated in predefined ways at predefined body sites. A plurality of simulation scenarios may be created for training purposes by using the pruned and scheduled stimulation signals.

At step 412, the scheduled signals are processed to obtain a response corresponding to each stimulation signal pick up site. In various embodiments, the response at any pick up body site is the weighted sum of all signals that are detectable at that site.

Within the training simulator, each level of connectivity in the nervous system model drives the following level with a synaptic model that accurately describes the impact of all other inputs, as well as generating locally the simulated output from that component. Ascending and descending nervous system pathways (peripheral nerves, cranial nerves, spinal cord, brainstem and brain) have known generators and pathways between the stimulation and final recording sites. Any nerve between the brain and the body only carries its signal part of the way. For example, stimulation is performed at a point A via path B to a recording point C. If path B is affected (either enhanced or diminished) at any point between A and C, then the response at C will be affected accordingly. In an example, SSEP stimulation of the left median nerve at the wrist at time zero will result in the stimulus being propagated afferently along the left median nerve, through the brachial plexus at a first time X (approximately 9-10 milliseconds latency with amplitude of 1-2 microvolts), through the cervical nerve roots, into the spinal cord at a second time Y (approximately 13-15 milliseconds latency with amplitude of 1-2 microvolts), through the brainstem and finally to the contralateral somatosensory cortex at a third time Z (approximately 18-20 milliseconds latency with amplitude of 1-3 microvolts). The response to stimulation of the left median nerve can be recorded at any point along the pathway, between stimulation at the wrist and recording at the contralateral somatosensory cortex. If the response was enhanced or diminished (i.e. reduced amplitude and/or increased latency) at the brachial plexus recording site, the subsequent proximal recording sites (i.e. cervical nerve roots, spinal cord, brainstem and contralateral somatosensory cortex) would also be enhanced or diminished in a similar manner. In some cases, the response terminates at a synapse where two nerves meet, and the signal propagates from the first nerve to the second nerve. This process adds delay, attenuation, amplification, modulation, and other effects, as well as generating a detectable electrical response. Embodiments of the present specification account for multiple parameters that affect the signal and the propagated response, and the 'modulated' propagated response is then used for subsequent calculations in the signal chain. Therefore, each level of connectivity in the nervous system model drives the following level with a synaptic model that accurately describes the impact of all other inputs, as well as generating locally the simulated output from that component.

Figure 4B:
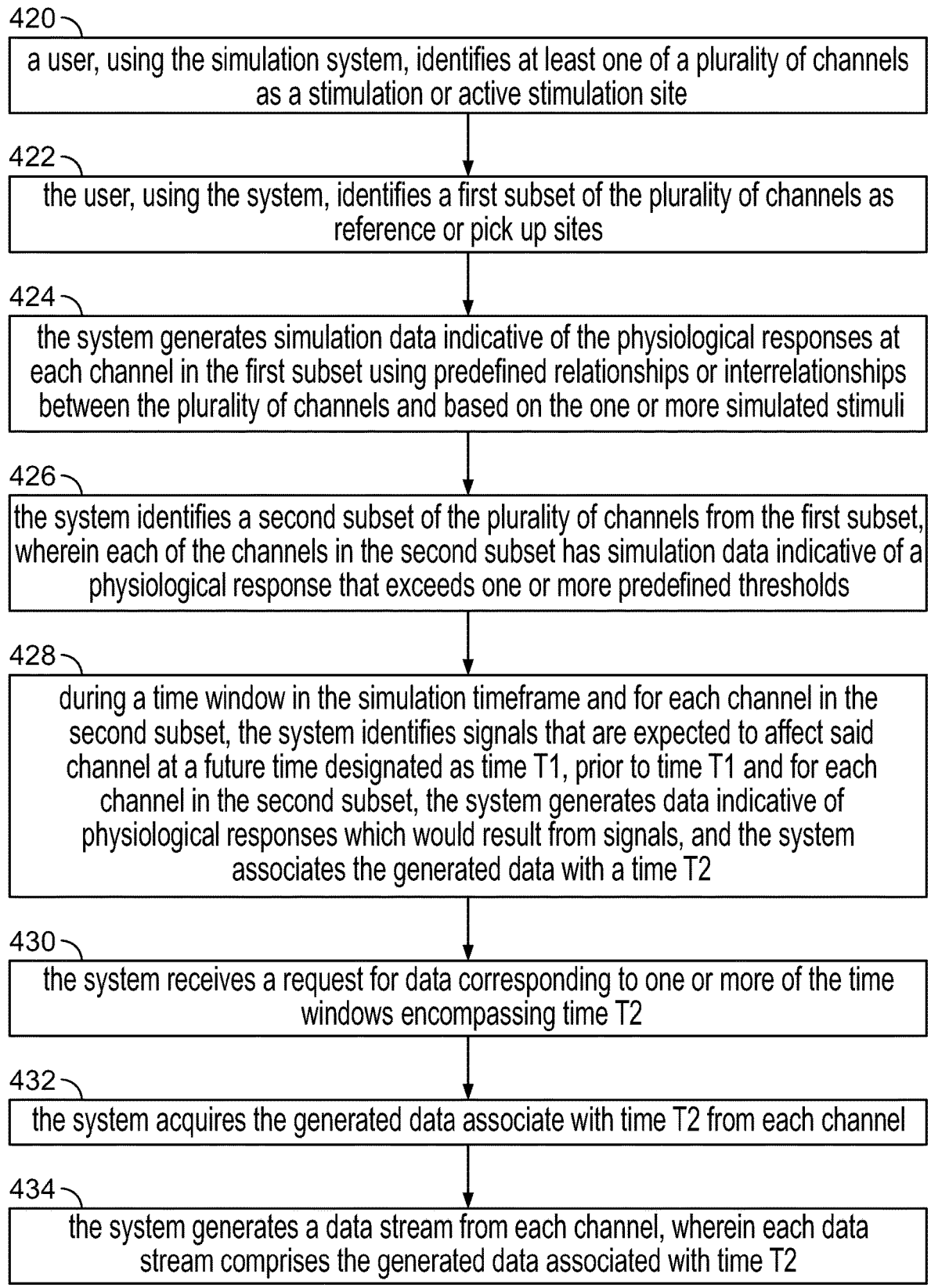
FIG. 4B is a flowchart illustrating the operational steps of an IONM training simulator, in accordance with another embodiment of the present specification.

FIG. 4B is a flowchart illustrating the operational steps of an IONM training simulator, in accordance with another embodiment of the present specification. The IONM training simulator comprises a simulation system in accordance with the embodiments of the present specification, configured to simulate a patient's physiological responses to one or more stimuli over a simulation timeframe, and comprising programmatic instructions stored in a tangible, non-transitory computer readable medium, wherein the programmatic instructions define a plurality of channels, each of said channels being virtually representative of an anatomical site of the patient, and wherein, when executed, the programmatic instructions are configured to simulate the physiological responses to the one or more stimuli.

At step 420, a user, using the simulation system, identifies at least one of a plurality of channels as a stimulation or active stimulation site, defined as a location where one or more stimuli is to be virtually applied to the patient. In various embodiments, the one or more stimuli comprise at least one of an electrical stimulation, an auditory stimulation (evoked potential), or visual stimulation (evoked potential). The user then, using the system, identifies a first subset of the plurality of channels as reference or pick up sites at step 422. The reference sites are defined as locations where physiological responses to the one or more simulated stimuli are to be determined. Steps 420 and 422 represent the initial steps of selecting stimulation and reference sites performed by the user.

At step 424, the system generates simulation data indicative of the physiological responses at each channel in the first subset using predefined relationships or interrelationships between the plurality of channels and based on the one or more simulated stimuli. In some embodiments, the relationships and interrelationships define a signal strength of a response at the channel. In embodiments, the relationships or interrelationships between the plurality of channels comprise distance and geometry, wherein geometry includes electrode orientation and muscle or nerve orientation, and the effects of obesity, neural anastomosis, and other atypical neural anatomies on signal strength, and distance is defined as the distance of an active stimulation site from a signal reference or pick up site. Then, at step 426, the system identifies a second subset of the plurality of channels from the first subset, wherein each of the channels in the second subset has simulation data indicative of a physiological response that exceeds one or more predefined thresholds. In some embodiments, not all of the channels in the first subset will have data indicative of a physiological response that exceeds the one or more predefined thresholds, and therefore the number of channels in the second subset will be less than the number of channels in the first subset. Steps 424 and 426 represent the pruning step of the simulation process. In embodiments, the remaining channels of the first subset not included in the identification of the second subset are identified as a third subset of the plurality of channels, and each of the channels of the third subset has simulation data indicative of the a physiological response that does not exceed the one or more predefined thresholds. The system in configured to not generate a data stream for channels in the third subset.

At step 428, the system generates data indicative of physiological responses at each channel in the second subset by: during each time window of a plurality of time windows within the simulation timeframe and for each channel in the second subset, identifying one or more signals that are expected to affect said channel at a future time designated as time T1; prior to future time T1 and for each channel in the second subset, generating data indicative of physiological responses which would result from the one or more signals that are expected to affect said channel at the future time T1; and associating the generated data with a time T2. In some embodiments, each time window is less than one second in duration. Step 428 represents the scheduling step of the simulation process by calculating expected responses, to at least one stimulus at an active stimulation site, at response or pick up sites before the time they would actually occur (T1), time stamping the calculated responses with a time window (T2) of when they would occur, and buffering or caching the calculated responses for presentation when the time window (T2) is requested by the system. In various embodiments, the one or more signals expected to affect the channel at future time T1 are a function of one or more of the following: the one or more simulated stimuli; a simulated injury to the patient; at least one simulated physiological response occurring at another channel prior to time T1; simulated interference from an electrosurgical instrument; a simulated positioning of a portion of the patient's body; simulated mains interference; a simulated electrocardiogram (EKG) signal; a simulated motion artifact signal; or, a simulated electromyography (EMG) signal. In some embodiments, the one or more signals expected to affect that channel at future time T1 are defined by at least one waveform having an amplitude exceeding a predefined threshold. In some embodiments, the one or more signals expected to affect that channel at future time T1 are defined by at least one waveform originating from another channel having a virtual distance exceeding a predefined threshold. In some embodiments, the system generates data indicative of physiological responses at each channel in the second subset by: during each time window within the simulation timeframe and for each channel in the second subset, identifying one or more global modulators that are expected to affect all channels in the second subset at a future time T1; and, prior to future time T1 and for each channel in the second subset, generating data indicative of physiological responses which would result from the global modulators that are expected to affect all channels in the second subset at the future time T1. In various embodiments, global modulators comprise at least one of a simulated temperature of the patient or a virtual administration of anesthesia to the patient.

At step 430, the system receives a request for data corresponding to one or more of the time windows encompassing time T2. The system acquires the generated data associate with time T2 from each channel at step 432. The system then generates a data stream from each channel at step 434, wherein each data stream comprises the generated data associated with time T2.

In some embodiments, the system further generates data indicative of physiological responses at each channel in the second subset by: during a second time window within the simulation timeframe and for each channel in the second subset, identifying a second set of one or more signals that are expected to affect said channel at a future time T3, wherein the second set of one or more signals are a function of at least some of the generated data associated with a time T2; prior to future time T3 and for each channel in the second subset, generating data indicative of physiological responses which would result from the second set of one or more signals; and associating the generated data with a time T4. In some embodiments, the system further receives a request for data corresponding to one or more of the time windows encompassing time T4; acquires the generated data associated with time T4 from each channel; and generates a data stream from each channel, wherein each data stream comprises the generated data associated with time T4.

Use Scenarios

In various embodiments, a trainee may use the simulator of the present specification for self-guided learning whereby the trainee adjusts parameters within a control panel to experience likely outcomes in a controlled environment, or simply "to see what happens." An instructor may use the simulator with one or more trainees by manipulating the control panel to simulate a series of events which may be achieved in a number of ways. For example, in an embodiment, an instructor starts a case (as recorder) and connects a second monitor and moves the control panel out of view, only displaying the recording screen to trainees. In another embodiment, a trainee starts a recording and the instructor connects to the case remotely acting as a reviewer. The trainee assigns the instructor as owner of the control panel and the instructor decides whether to hide the control panel from other connected users (the trainee doing the recording and others).

Figure 5:
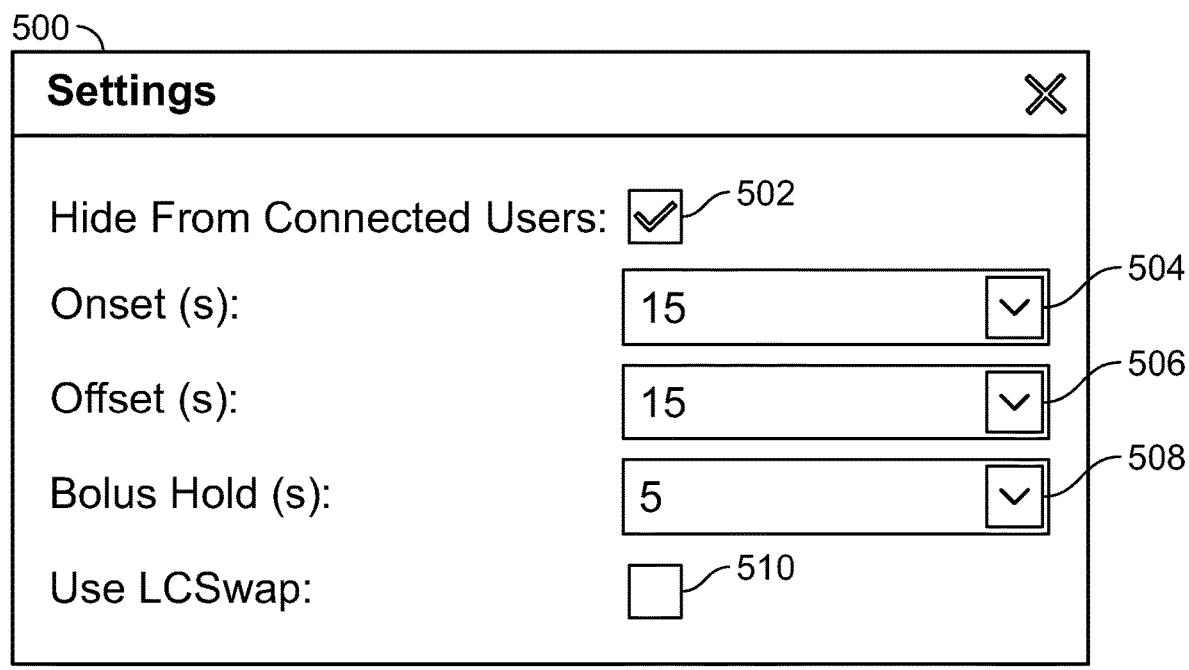
FIG. 5 illustrates an exemplary user interface for setting timing of effects, in accordance with an embodiment of the present specification.

In an embodiment, timing of effects, such as but not limited to, onset, offset, and bolus duration for a simulation can be set by the user by using one or more software user interfaces of the training simulator. FIG. 5 illustrates an exemplary user interface for setting timing of effects, in accordance with an embodiment of the present specification. In an embodiment, a settings window 500 may be accessed by accessing simulator settings gear in a top right of a control panel header. In some embodiments, settings window 500 provides options to allow an owner of the control panel to hide the control panel from connected users 502, set onset timing 504, set offset timing 506, set bolus hold timing 508, and activate a switch matrix 510 to independently assign outputs as cathode or anode.

Figure 6:
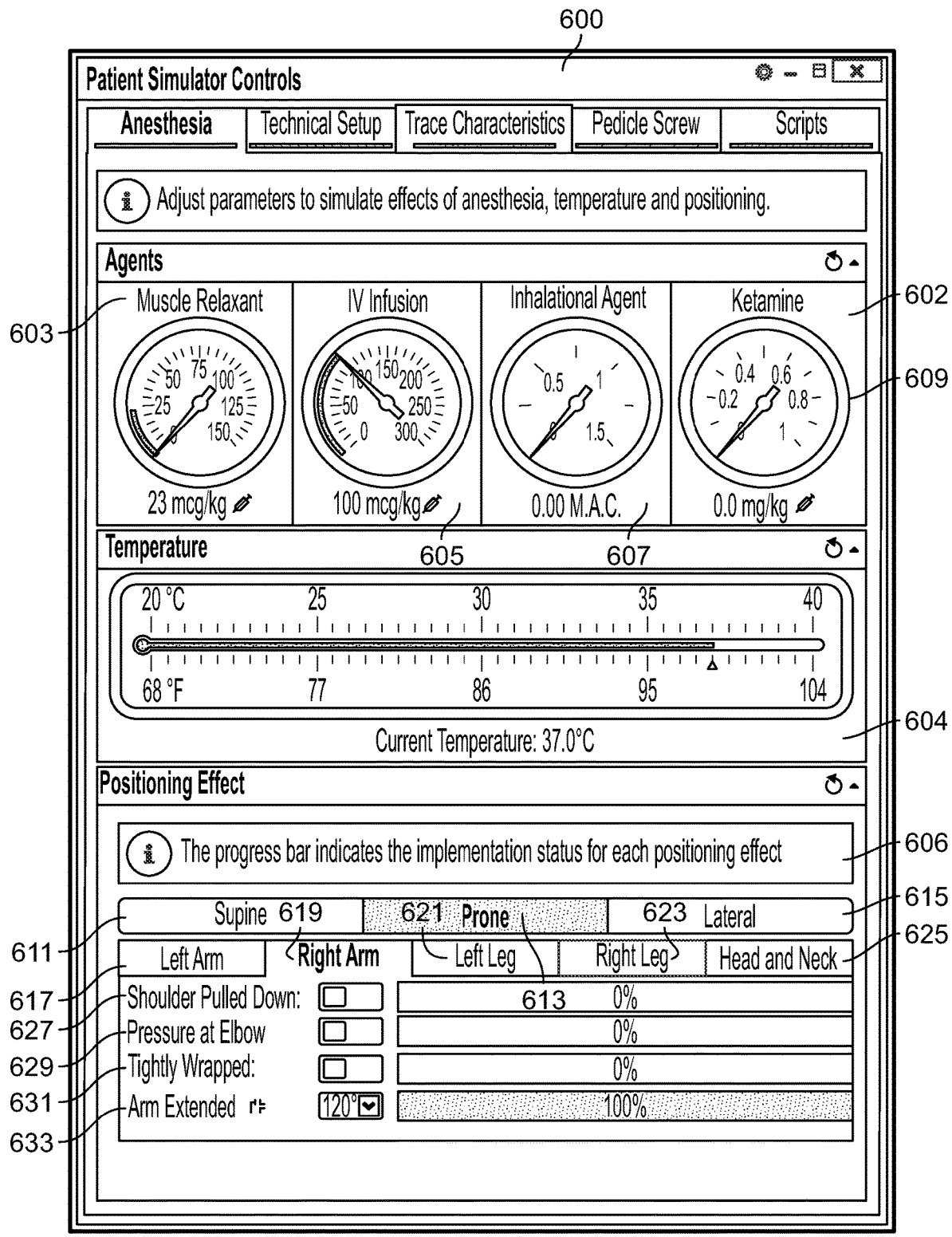
FIG. 6 illustrates an exemplary user interface for simulating effects of anesthesia agents, temperature, and positioning, on a patient undergoing IONM, in accordance with an embodiment of the present specification.

In an embodiment, users may simulate effects of anesthesia agents, temperature, and positioning on a patient undergoing IONM by using one or more software user interfaces of the training simulator. FIG. 6 illustrates an exemplary user interface for simulating effects of anesthesia agents, temperature, and positioning, on a patient undergoing IONM, in accordance with an embodiment of the present specification. Control window 600 comprises an agents section 602 with sub-windows for applying or adjusting anesthetic agents such as a muscle relaxant 603, IV infusion 605, inhalational agent 607 and/or ketamine 609 being given to the patient. In embodiments, control window 600 also includes a temperature section 604 for adjusting temperature to simulate warming or cooling the patient. In embodiments, control window 600 also includes a positioning effect section 606 for setting a patient's position to a plurality of different positions, including but not limited to 'supine' 611, 'prone' 613, and 'lateral' 615. Positioning effect section 606 also allows a user to applying positioning effects for different body parts, including but not limited to 'left arm' 617, 'right arm' 619, 'left leg' 621, 'right leg' 623, and 'head and neck' 625. Positioning effect section 606 also allows a user to applying positioning effects to specific extremities, including but not limited to, for a patient's arm, 'shoulder pulled down' 627, 'pressure at elbow' 629, 'tightly wrapped' 631, and 'arm extended' 633. A user may apply multiple effects to one or more extremities of the patient to observe the cumulative simulated effect. In the example simulation set up shown in the window 600, a bolus of muscle relaxant has been applied, IV infusion is running, temperature is unchanged (set to default) and the simulated patient is prone with their right arm fully extended.

Figure 7:
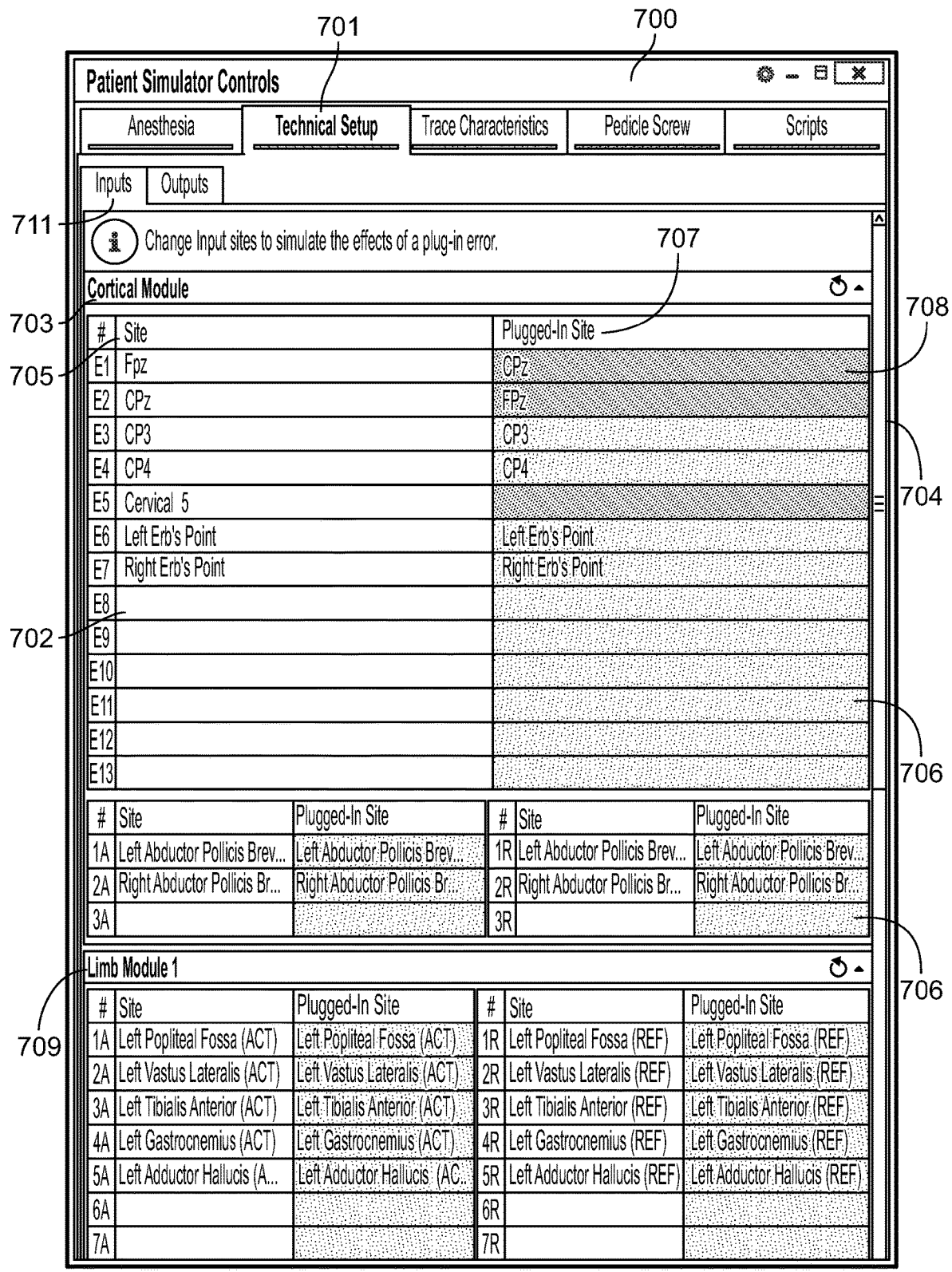
FIG. 7 illustrates an exemplary user interface for simulating effects of plug-in error or empty input on a patient undergoing IONM, in accordance with an embodiment of the present specification.

In an embodiment, the training simulator allows users to swap or remove input and output stimulation sites to simulate the effect of a plug-in error (i.e. electrodes plugged in to the wrong amplifier or stimulator position) or empty input (i.e. an open channel) on a patient undergoing IONM by using one or more software user interfaces of the training simulator. FIG. 7 illustrates an exemplary user interface for simulating effects of plug-in error or empty input on a patient undergoing IONM, in accordance with an embodiment of the present specification. A left side 702 of a cortical module 703 of an inputs tab 711 of a technical setup tab 701 of a simulator controls window 700 shows the inputs and outputs that are programmed in a procedure template in use, wherein the actual site 705 cells have white backgrounds. On the right side 704 of the window, users can remove an electrode by selecting the cell and clicking 'X' or using the drop-down to select a plugged-in site 707 that is the same or different from what is the actual site 705 in the procedure setup. A green cell background 706 indicates the simulator input/output matches that of the procedure setup. A red cell background 708 indicates there is a mismatch between the simulator input/output and that of the procedure setup. In the example simulation set up shown FIG. 7, 'CPz' and 'Fpz' are plugged in backwards and 'Cervical 5' is unplugged. Similar functions are enabled for a limb module 1 709.

Figure 8:
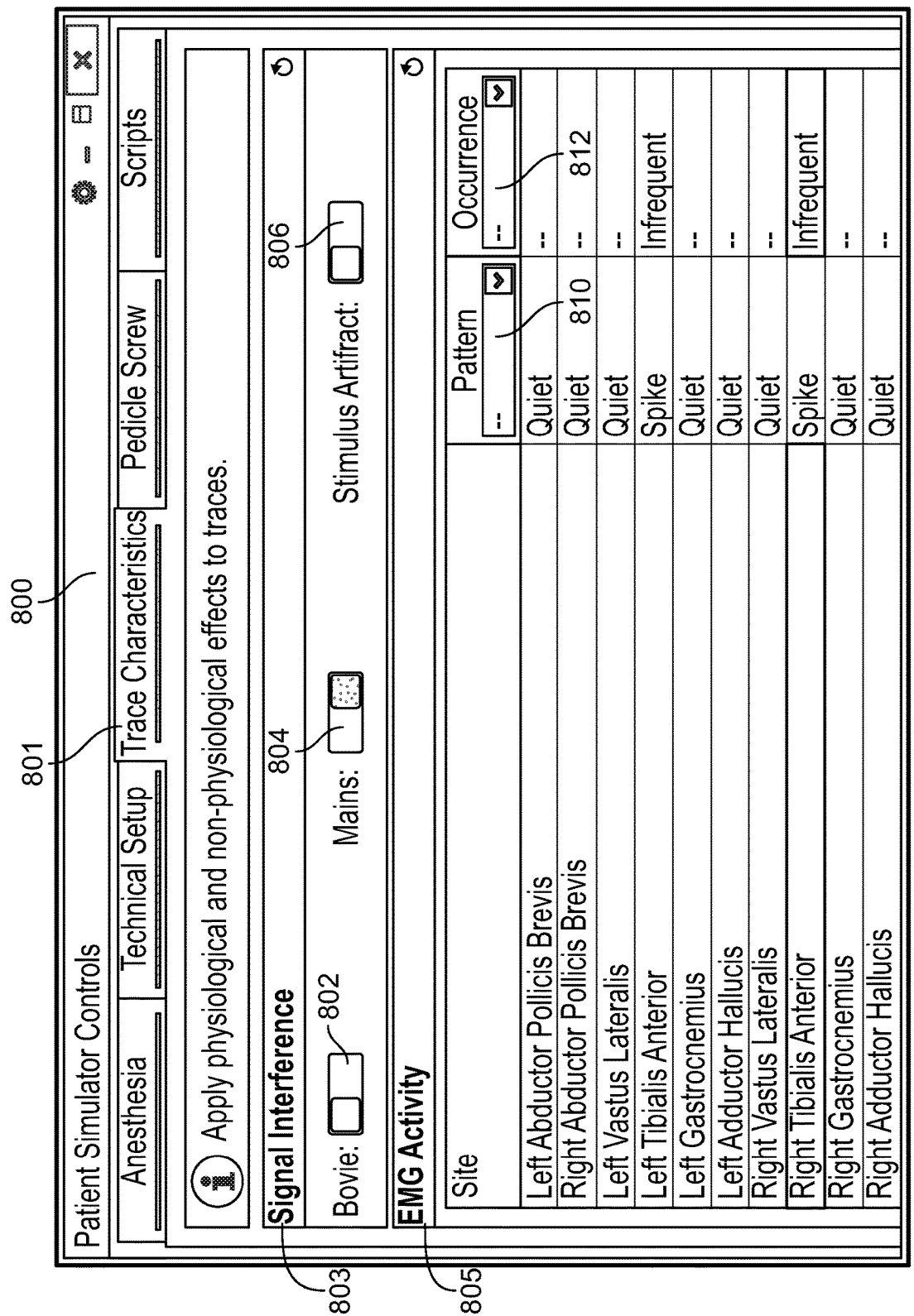
FIG. 8 illustrates an exemplary user interface for simulating effects of physiological and non-physiological effects on traces on a patient undergoing IONM, in accordance with an embodiment of the present specification.

In an embodiment, the training simulator allows users to simulate physiological and non-physiological effects on traces on a patient undergoing IONM by using one or more software user interfaces of the training simulator. FIG. 8 illustrates an exemplary user interface for simulating effects of physiological and non-physiological effects on traces on a patient undergoing IONM, in accordance with an embodiment of the present specification. By using signal interference section 803 of trace characteristics tab 801 of simulator controls window 800 signal interference effect of electrosurgery can be simulated by toggling the control 'bovie' 802 on/off. Turning on the control 'mains' 804 simulates the effect of injecting 50 or 60 Hz noise, depending on the system settings. The control 'stimulus artifact' 806 enables turning excessive stimulus shock artifact on or off. Simulation controls window 800 displays any patient muscle defined in the procedure setup in EMG activity section 805. A 'quiet' pattern of the muscles is default, while the drop-down menu 'pattern' 810 may be used to choose 'spike' or 'burst' pattern for one or more muscles. Drop down menu 'occurrence' 812 may be used to define how often the EMG activity will be observed. In the example simulation set up shown in FIG. 800, 'mains' noise (60 Hz) is turned on and left and right tibialis anterior muscles are infrequently spiking.

In an embodiment, the training simulator allows users to simulate pedicle screw stimulation with varying levels of pedicle screw integrity on a patient undergoing IONM by using one or more software user interfaces of the training simulator. FIG. 9 illustrates an exemplary user interface for simulating pedicle screw stimulation with varying levels of pedicle screw integrity on a patient undergoing IONM, in accordance with an embodiment of the present specification. Pedicle screw tab 901 of simulation controls window 900 comprises an anatomical spine section 902 wherein a user may click on an illustration of an anatomical spine 904 to populate a list of stimulation locations in pedicle stim section 906. The user may also click and drag horizontal bars 907 to adjust the pedicle screw integrity level 908 of pedicle screw locations section 905 for different pedicle screw locations 909, for example, 'left pedicle sites' 910 and 'right pedicle sites' 912. In the example simulation set up shown in FIG. 9, left and right L2, L3 and L4 are set up for stimulation. Left L4 is set to have a low threshold.

Figure 10:
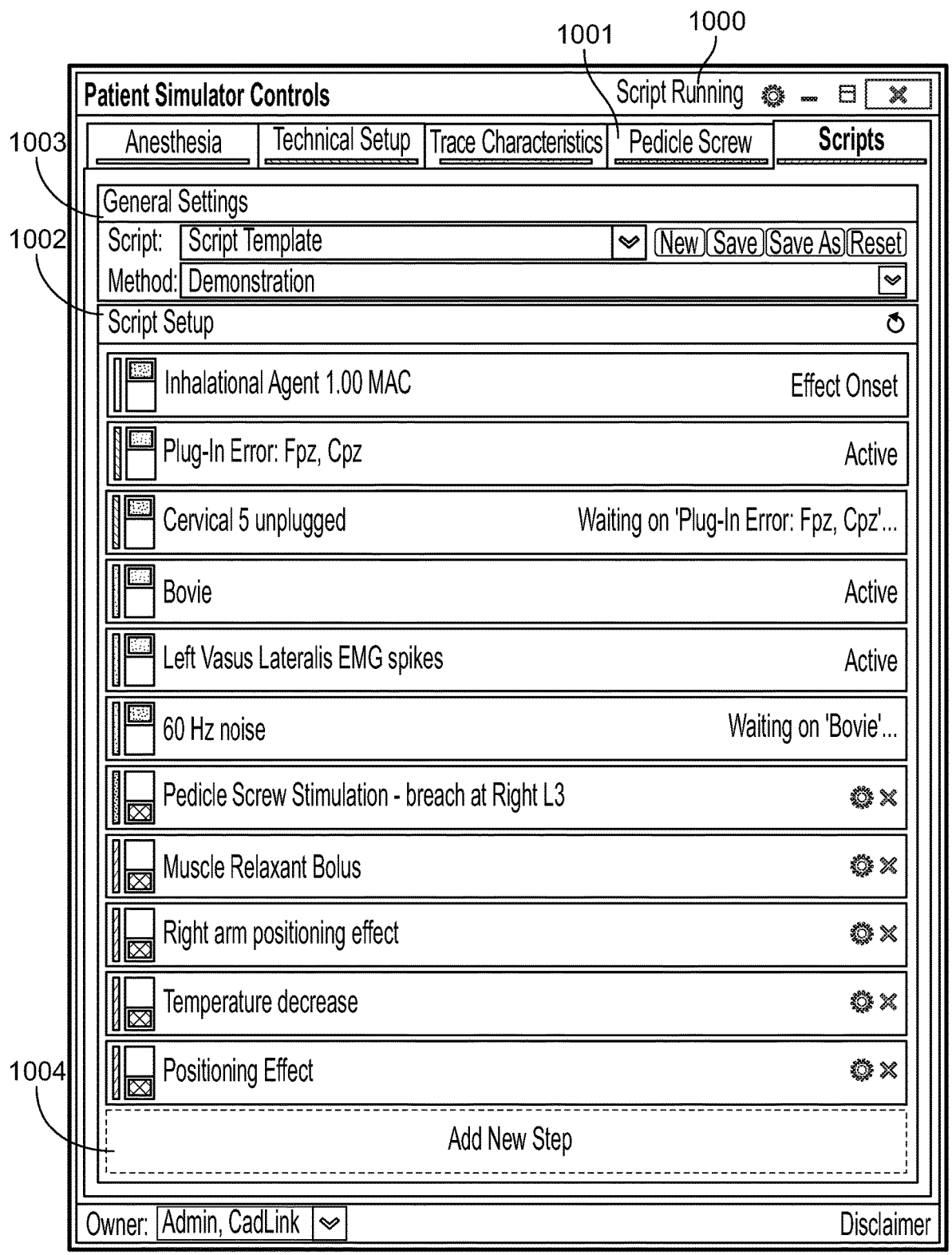
FIG. 10 illustrates an exemplary user interface for setting up simulator controls for simulating a patient undergoing IONM, in accordance with an embodiment of the present specification.

In an embodiment, trainees or teachers may create and manage simulator scripts which are useful for planning and demonstrating a series of events and may even be used for assessment purposes. The same script can be used for demonstration and assessment purposes. FIG. 10 illustrates an exemplary user interface for setting up simulator controls for simulating a patient undergoing IONM, in accordance with an embodiment of the present specification. Scripts tab 1001 of simulator controls window 1000 includes a general settings section 1003 and enables a user to set up simulator controls for simulating a patient undergoing IONM by using a 'script setup' section 1002, wherein effects such as but not limited to, anesthetic agent, plug-in error, EMG control, positioning, and temperature may be manipulated. A user may add effects to a stimulator script by using the 'add new step' section 1004. In various embodiments, the owner of the control panel may use a simulation script for assessing a trainee, wherein the simulator software of the present specification allows the script to run through the script's steps in order and at a user-defined cadence. The owner of the control panel can mark whether an effect was correctly identified by the trainee and use that information to focus additional training efforts.

The above examples are merely illustrative of the many applications of the system and method of present specification. Although only a few embodiments of the present specification have been described herein, it should be understood that the present specification might be embodied in many other specific forms without departing from the spirit or scope of the specification. Therefore, the present examples and embodiments are to be considered as illustrative and not restrictive, and the specification may be modified within the scope of the appended claims.

We claim:

1. A system for simulating a patient's physiological responses to one or more stimuli over a simulation timeframe, wherein the system comprises programmatic instructions stored in a tangible, non-transitory computer readable medium, wherein the programmatic instructions define a plurality of channels, each of said channels being virtually representative of an anatomical site of the patient, and wherein, when executed, the programmatic instructions:
 identify at least one of the plurality of channels as a stimulation site;
 identify a first subset of the plurality of channels as reference sites;
 generate simulation data indicative of the physiological responses at each channel in the first subset using predefined relationships between the plurality of channels and based on the one or more simulated stimuli;
 identify a second subset of the plurality of channels from the first subset, wherein each of the channels in the second subset has simulation data indicative of a physiological response that exceeds one or more predefined thresholds;
 generate data indicative of physiological responses at each channel in the second subset by:
  during each of a time window of a plurality of time windows within the simulation timeframe and for each channel in the second subset, identifying one or more signals that are expected to affect said channel at a future time T1;
  prior to future time T1 and for each channel in the second subset, generating data indicative of physiological responses which would result from the one or more signals that are expected to affect said channel at the future time T1; and
  associating the generated data with a time T2;
 receive a request for data corresponding to one or more of the time windows encompassing time T2;
 acquire the generated data associated with time T2 from each channel; and
 generate a data stream from each channel, wherein each data stream comprises the generated data associated with time T2.

2. The system of claim 1, wherein the stimulation site is a location where the one or more stimuli is to be virtually applied to the patient.

3. The system of claim 2, wherein the one or more stimuli is at least one of an electrical stimulation, an auditory stimulation, or a visual stimulation.

4. The system of claim 1, wherein the reference sites are locations where physiological responses to the one or more simulated stimuli are to be determined.

5. The system of claim 1, wherein, when executed, the programmatic instructions identify, from the first subset, a third subset of the plurality of channels, wherein each of the channels in the third subset has simulation data indicative of a physiological response that does not exceed one or more predefined thresholds.

6. The system of claim 5, wherein, when executed, the programmatic instructions do not generate a data stream from each channel in the third subset.

7. The system of claim 1, wherein a number of channels in the second subset is less than a number of channels in the first subset.

8. The system of claim 1, wherein the one or more signals that are expected to affect said channel at a future time T1 are a function of the one or more simulated stimuli.

9. The system of claim 1, wherein the one or more signals that are expected to affect said channel at a future time T1 are a function of a simulated injury to the patient.

10. The system of claim 1, wherein the one or more signals that are expected to affect said channel at a future time T1 are a function of at least one simulated physiological response occurring at another channel prior to time T1.

11. The system of claim 1, wherein the one or more signals that are expected to affect said channel at a future time T1 are defined by at least one waveform having an amplitude exceeding a predefined threshold.

12. The system of claim 1, wherein the one or more signals that are expected to affect said channel at a future time T1 are a function of simulated interference from an electrosurgical instrument.

13. The system of claim 1, wherein the one or more signals that are expected to affect said channel at a future time T1 are a function of a simulated positioning of a portion of the patient's body.

14. The system of claim 1, wherein the one or more signals that are expected to affect said channel at a future time T1 are a function of simulated mains interference.

15. The system of claim 1, wherein the one or more signals that are expected to affect said channel at a future time T1 are defined by at least one waveform originating from another channel having a virtual distance exceeding a predefined threshold.

16. The system of claim 1, wherein the one or more signals that are expected to affect said channel at a future time T1 are defined by a simulation electrocardiogram (EKG) signal.

17. The system of claim 1, wherein the one or more signals that are expected to affect said channel at a future time T1 are defined by a simulated motion artifact signal.

18. The system of claim 1, wherein the one or more signals that are expected to affect said channel at a future time T1 are defined by a simulated electromyography (EMG) signal.

19. The system of claim 1, wherein, when executed, the programmatic instructions further generate data indicative of physiological responses at each channel in the second subset by:
during each time window within the simulation timeframe and for each channel in the second subset, identifying one or more global modulators that are expected to affect all channels in the second subset at a future time T1; and
prior to time T1 and for each channel in the second subset, generating data indicative of physiological responses which would result from the global modulators that are expected to affect all channels in the second subset at future time T1.

20. The system of claim 19, wherein the one or more global modulators that are expected to affect all channels in the second set at a future time T1 comprise a simulated temperature of the patient.

21. The system of claim 19, wherein the one or more global modulators that are expected to affect all channels in the second subset a future time T1 comprise a virtual administration of anesthesia to the patient.

22. The system of claim 1, wherein the time window is less than 1 second.

23. The system of claim 1 wherein, when executed, the programmatic instructions further generate data indicative of physiological responses at each channel in the second subset by:
during a second time window within the simulation timeframe and for each channel in the second subset, identifying a second set of one or more signals that are expected to affect said channel at a future time T3, wherein the second set of one or more signals are a function of at least some of the generated data associated with a time T2;
prior to future time T3 and for each channel in the second subset, generating data indicative of physiological responses which would result from the second set of one or more signals; and
associating the generated data with a time T4.

24. The system of claim 23 wherein, when executed, the programmatic instructions further receive a request for data corresponding to one or more of the time windows encompassing time T4;
acquire the generated data associated with time T4 from each channel; and
generate a data stream from each channel, wherein each data stream comprises the generated data associated with time T4.

* * * * *